United States Patent [19]

Baker et al.

[11] Patent Number: 5,405,853
[45] Date of Patent: Apr. 11, 1995

[54] THIADIAZOLES USEFUL IN THE TREATMENT OF SENILE DEMENTIA

[75] Inventors: Raymond Baker, Much Hadham; Angus M. MacLeod, Bishop's Stortford; John Saunders, Bishop's Stortford; Kevin Merchant, Bishop's Stortford, all of England

[73] Assignee: Merck Sharpe & Dohme Ltd., Hoddesdon, England

[21] Appl. No.: 166,656

[22] Filed: Dec. 13, 1993

Related U.S. Application Data

[63] Continuation of Ser. No. 941,461, Sep. 8, 1992, abandoned, which is a continuation of Ser. No. 621,124, Dec. 3, 1990, abandoned.

[30] Foreign Application Priority Data

Sep. 10, 1987 [GB] United Kingdom ............... 8721342
Jan. 27, 1988 [GB] United Kingdom ............... 8801758
May 23, 1988 [GB] United Kingdom ............... 8812145
Jul. 20, 1988 [GB] United Kingdom ............... 8817311

[51] Int. Cl.$^6$ ................... C07D 413/14; A61K 31/33
[52] U.S. Cl. ...................... 514/299; 514/305; 514/312; 514/361; 546/112; 546/133; 546/277; 548/128
[58] Field of Search ............... 548/128; 546/112, 133, 546/277; 514/361, 305, 342, 299

[56] References Cited

U.S. PATENT DOCUMENTS

| | | | |
|---|---|---|---|
| 3,912,495 | 10/1975 | Moser et al. | 548/125 |
| 4,301,069 | 11/1981 | Weaver et al. | 548/125 |
| 4,645,525 | 2/1987 | Forster et al. | 548/125 |
| 4,968,691 | 11/1990 | Orlek | 548/125 |

FOREIGN PATENT DOCUMENTS

| | | |
|---|---|---|
| 2247266 | 4/1973 | Denmark . |
| 3038636 | 5/1982 | Denmark . |
| 0020161 | 12/1980 | European Pat. Off. . |
| 0018497 | 4/1982 | European Pat. Off. . |
| 0239309 | 9/1987 | European Pat. Off. . |
| 0261763 | 3/1988 | European Pat. Off. . |

OTHER PUBLICATIONS

Zbirovsky, M., et al Chem. Abs. 76 (1972) 113135k.
Potts, Comprehensive Meterocyclic Chemistry pp. 492–501 (1989).

*Primary Examiner*—Robert Gerstl
*Attorney, Agent, or Firm*—Robert J. North; Joseph F. DiPrima; Melvin Winokur

[57] ABSTRACT

A class of novel thiadiazoles, substituted on one of the ring carbon atoms with a non-aromatic azacyclic or azabicyclic ring system, and substituted on the other ring carbon atom with a substituent of low lipophilicity, or a hydrocarbon substituent; are potent muscarinic agonists, and have good CNS penetrability. The compounds are therefore useful in the treatment of neurological and mental illnesses, and are also of benefit in the treatment of severe painful conditions.

8 Claims, No Drawings

THIADIAZOLES USEFUL IN THE TREATMENT OF SENILE DEMENTIA

This is a continuation of application Ser. No. 07/941,461, filed on Sep. 8, 1992, now abandoned, which is a continuation of application Ser. No. 07/621,124, filed Dec. 3, 1990, now abandoned.

The present invention relates to a class of substituted thiadiazole compounds which stimulate central muscarinic acetylcholine receptors and therefore are useful in the treatment of neurological and mental illnesses whose clinical manifestations are due to cholinergic deficiency. Such diseases include presenile and senile dementia (also known as Alzheimer's disease and senile dementia of the Alzheimer type respectively), Huntington's chorea, tardive dyskinesia, hyperkinesia, mania and Tourette Syndrome. Alzheimer's disease, the most common dementing illness, is a slowly progressive neurological disorder characterised by marked deficits in cognitive functions including memory, attention, language and visual perception capabilities. The compounds of this invention are also useful analgesic agents and therefore useful in the treatment of severe painful conditions such as rheumatism, arthritis and terminal illness.

Compounds capable of enhancing muscarinic cholinergic transmission in the cortex should be beneficial in reversing the cholinergic deficiency in Alzheimer's disease and other diseases related to cholinergic dysfunction. However, most muscarinic ligands, including acetylcholine itself, are quaternary ammonium compounds incapable of penetrating the blood-brain barrier to any clinically significant extent following peripheral (e.g. oral) administration. Such agents fail to stimulate the desired central sites but instead induce undesired side-effects mediated exclusively by peripherally-located muscarinic acetylcholine receptors.

The thiadiazole compounds of the present invention stimulate cholinergic transmission but, being either secondary or tertiary amines with physiochemical properties (lipophilicity and pKa) consistent with CNS penetrability, can stimulate those central sites implicated in neurodegenerative disorders. It is believed that the enhancement of cholinergic transmission demonstrated by the compounds of this invention is achieved either directly by stimulating postsynaptic receptors, or indirectly by potentiating acetylcholine release.

The present invention provides a thiadiazole, or a salt or prodrug thereof, which thiadiazole is substituted on one of the ring carbon atoms thereof with a non-aromatic azacyclic or azabicyclic ring system; and substituted on the other ring carbon with a substituent of low lipophilicity, or a hydrocarbon substituent.

Although a class of thiadiazole compounds having a pyridyl substituent on a ring carbon atom are disclosed in European Patent Specification No. 116515 as pesticides, there is no suggestion therein of any non-aromatic ring, or of any activity other than pesticidal activity.

In addition, EP-A-0261763, which was published on 30 Mar. 1988, describes a class of compounds which includes thiadiazoles substituted on the thiadiazole ring by a group of formula

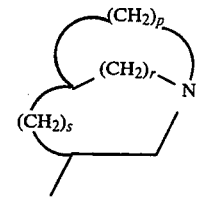

in which p represents an integer of 2 to 4; r represents an integer of 1 or 2; and s represents 0 or 1; such that when (p,r,s) is (2,2,0) or (2,2,1) the thiadiazole nucleus is optionally C-substituted by a methyl group, and when (p,r,s) is (2,1,0), (2,1,1) or (3,1,0) the thiadiazole nucleus is optionally C-substituted by $C_{1-2}$ alkyl; and wherein such thiadiazoles having two asymmetric centres have the exo stereochemical configuration, i.e. the configuration in which the thiadiazole ring and the $(CH_2)_r$ bridge are on the same side of the plane of the molecule which contains both bridgehead atoms and the ring carbon bonded to the thiadiazole ring. Example 7 of EP-A-0261763 purports to describe the preparation of (+)-3-(3-methyl-1,2,4-thiadiazol-5-yl)-1-azabicyclo[2.2.2]octane; none of the other Examples in this document purports to describe the preparation of a thiadiazole. However, the information in Example 7 of EP-A-0261763 does not in fact enable the title compound of Example 7 of EP-A-0261763 to be prepared and separated. From this it follows that the information contained in EP-A-0261763 does not enable any such thiadiazoles to be prepared and separated.

The novel compounds of this invention may be represented by structural formula IA, IB or IC:

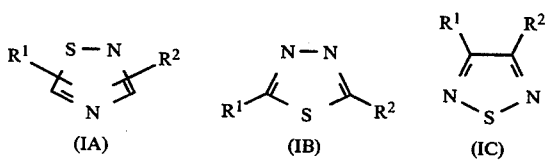

or a salt or prodrug thereof; wherein $R^1$ represents a non-aromatic azacyclic or azabicyclic ring system; and $R^2$ represents hydrogen, halogen, $-CF_3$, $-OR^7$, $-SR^7$, $-NR^7R^8$, $-NHOR^7$, $-NHNH_2$, $-CN$, $-CO_2R^7$, $-CONR^7R^8$, or a substituted or unsubstituted, saturated or unsaturated hydrocarbon group; wherein $R^7$ and $R^8$ independently represent hydrogen or $C_{1-2}$ alkyl.

Preferably the thiadiazole ring is a 1,2,4-thiadiazole of formula IA.

The azacyclic or azabicyclic ring system is a non-aromatic ring system containing one nitrogen atom as the sole heteroatom. Suitably the ring system contains from 4 to 10 ring atoms, preferably from 5 to 8 ring atoms. Preferably, the ring system contains a tertiary amino nitrogen atom in a caged structure. The bicyclic systems may be fused, spiro or bridged. Preferably, the nitrogen atom is at a bridgehead in a bicyclic system. Examples of suitable ring systems for the group $R^1$ include the following:

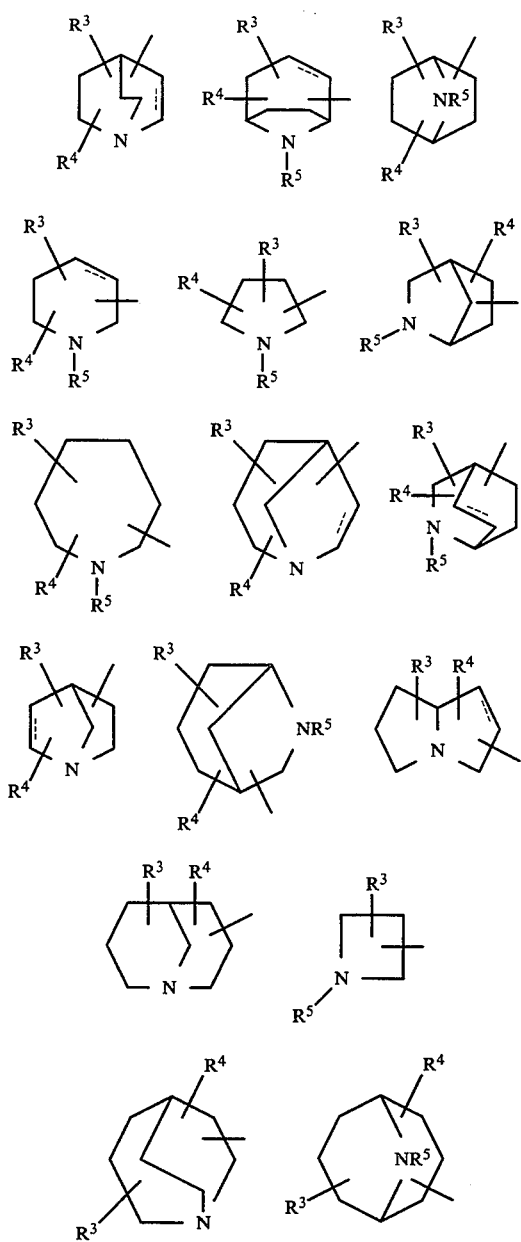

wherein the broken line represents an optional chemical bond;

the substituents $R^3$ and $R^4$ may be present at any position, including the point of attachment to the thiadiazole ring, and independently represent hydrogen, $C_{1-4}$ alkyl, halo, $C_{1-4}$ alkoxy, hydroxy or carboxy; or $R^3$ and $R^4$ together represent carbonyl; and the group $R^5$ represents hydrogen or $C_{1-4}$ alkyl.

It will be appreciated that the nitrogen atom in the azacyclic or azabicyclic ring system will carry a lone pair of electrons.

Suitably the group $R^3$ is hydrogen or methyl; and $R^4$ is hydrogen, methyl or hydroxy. Preferably one or both of $R^3$ and $R^4$ is hydrogen.

Preferably the group $R^5$ represents hydrogen or methyl.

Suitably the azacyclic or azabicyclic ring system is a pyrrolidine, piperidine, tetrahydropyridine, azanorbor-nane, quinuclidine, isoquinuclidine or azabicyclo[3.2.1]octane ring system. Preferred values for the azacyclic or azabicyclic ring system are tetrahydropyridine, quinuclidine and 1-azanorbornane, in particular either unsubstituted or substituted with methyl or hydroxy.

The substituent $R^2$ on the thiadiazole ring may be a substituent of low lipophilicity. The term "low lipophilicity" is intended to indicate that the group has a Rekker f value (hydrophobic fragment constant; see R. F. Rekker, "The Hydrophobic Fragmental Constant", Elsevier, 1977) of not greater than 1.5. For example, the methyl group has a value of 0.7 and the ethyl group a value of 1.26.

Thus the substituent of low lipophilicity, represented by the group $R^2$ in formula IA, IB and IC, may be, for example hydrogen, halogen, $-CF_3$, $-OR^7$, $-SR^7$, $-NR^7R^8$, $-NHOR^7$, $-NHNH_2$, $-CN$, $-CO_2R^7$, $-CONR^7R^8$, $C_{2-5}$ alkenyl, $C_{2-5}$ alkynyl, $C_{1-2}$ alkyl, or $C_{1-2}$ alkyl substituted with $-OR^7$, $-NR^7R^8$, $-SR^7$, $-CO_2R^7$, $-CONR^7R^8$ or halogen; wherein $R^7$ and $R^8$ independently represent hydrogen or $C_{1-2}$ alkyl.

Alternatively the group $R^2$ may represent an optionally substituted saturated hydrocarbon group having at least three carbon atoms, or unsaturated hydrocarbon group having at least 6 carbon atoms.

Thus when the group $R^2$ is a hydrocarbon substituent, it may be $C_{1-15}$ alkyl, $C_{2-15}$ alkenyl, $C_{2-15}$ alkynyl, aryl or aralkyl. The alkyl, alkenyl or alkynyl groups may be straight, branched or cyclic groups. Suitably the alkyl group comprises from 1 to 6 carbon atoms. The hydrocarbon group may carry one or more substituents. Suitable substituent groups for the hydrocarbon group $R^2$ include halogen, $-OR^6$, $-CF_3$, $-NR^6R^9$, $-NO_2$, optionally substituted aryl, optionally substituted heteroaryl, keto, $-SR^6$, $-SOR^6$, $-SO_2R^6$, $-CO_2R^6$ and $-CONR^6R^9$; wherein $R^6$ is hydrogen or $C_{1-6}$ alkyl, and $R^9$ is hydrogen, $C_{1-6}$ alkyl or $-COCH_3$.

Preferred substituents for the hydrocarbon group $R^2$ include phenyl, methylcarbonyloxy, hydroxy and methoxy.

Substituents most suitable for the aryl and heteroaryl groups include chloro, bromo, methoxy, $C_{1-6}$ alkyl, methoxycarbonyl, trifluoromethyl, nitro and $-NR^6R^7$.

Preferably the group $R^2$ is hydrogen, halogen, $-CF_3$, $-OR^7$, $-SR^7$, $-NR^7R^8$, $-NHNH_2$, $-CN$, $-CO_2R^7$, $-CONR^7R^8$, phenyl($C_{1-3}$)alkyl, $C_{3-6}$ cycloalkyl, adamantyl, $C_{2-6}$ alkenyl, $C_{2-6}$ alkynyl, $C_{1-6}$ alkyl, or $C_{1-6}$ alkyl substituted with $-OR^6$, $-NHR^6$, $-SR^6$, $-CO_2R^6$, $-CON(R^6)_2$ or halogen. Particular values of the group $R^2$ are hydrogen, methyl, ethyl, n-propyl, isopropyl, cyclopropyl, t-butyl, phenyl, benzyl, 1-phenylethyl, adamantyl, amino, methylamino, ethylamino, dimethylamino, methoxy, methylthio, methoxycarbonyl and ethoxycarbonyl. Preferred values of the group $R^2$ are hydrogen, methyl, ethyl, cyclopropyl, amino and dimethylamino.

One class of groups $R^2$ comprises methyl, ethyl, n-propyl, isopropyl, cyclopropyl or ethenyl, optionally substituted by one or more substituents selected from phenyl, acetoxy, keto, hydroxy and methoxy. A preferred group $R^2$ has the structure:

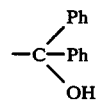

One group of prodrugs of compounds of this invention have a substituent on the thiadiazole ring which is hydrolysable in vivo to an amino group.

Groups which are hydrolysable in vivo to an amino group on the compounds of this invention may be readily ascertained by administering the compound to a human or animal and detecting, by conventional analytical techniques, the presence of the corresponding compound having an amino substituent in the urine of a human or animal. Examples of such groups include, for example, amido and urethane substituents, in particular a group of formula —NH.Q, wherein Q represents CHO, COR or $CO_2R$, and R represents an optionally substituted hydrocarbon group.

In this context, the hydrocarbon group R includes groups having up to 20 carbon atoms, suitably up to 10 carbon atoms, conveniently up to 6 carbon atoms. Suitable groups R include $C_{1-9}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, and aryl($C_{1-6}$)alkyl. The alkyl group R may be straight or branched chain and may contain, for example, up to 12 carbon atoms, suitably from 1 to 6 carbon atoms. In particular the group may be substituted methyl, ethyl, n- or iso-propyl, n-, sec-, iso- or tert-butyl, n- or iso-heptyl, or n- or iso-octyl. Suitable cycloalkyl groups include cyclopentyl and cyclohexyl. The aryl group R includes phenyl and naphthyl optionally substituted with up to five, preferably up to three, substituent groups.

One sub-class of compounds within the scope of the present invention is represented by formula II:

wherein $R^1$ and $R^2$ are as defined above; in particular wherein $R^1$ represents pyrrolidine, quinuclidine, tetrahydropyridine, piperidine, dehydrotropane, pyrrolizidine, azanorbornane or isoquinuclidine, any of which groups $R^1$ may be optionally substituted with $C_{1-3}$ alkyl, or hydroxy; and $R^2$ represents hydrogen, $C_{1-6}$ alkyl (preferably methyl or ethyl), $C_{3-6}$ cycloalkyl (preferably cyclopropyl), amino or dimethylamino. Preferably $R^1$ represents quinuclidine, tetrahydropyridine or 1-azanorbornane.

Specific compounds within the scope of the present invention include:

3-[5-(3-methyl-1,2,4-thiadiazol)-yl]pyrrolidine;
1-methyl-3-[5-(3-methyl-1,2,4-thiadiazol)-yl]-pyrrolidine;
3-[5-(3-methyl-1,2,4-thiadiazol)-yl]quinuclidine;
3-[5-(3-methyl-1,2,4-thiadiazol)-yl]-1-azabicyclo[2.2.1]heptane;
3-[5-(3-phenyl-1,2,4-thiadiazol)-yl]quinuclidine;
3-[5-(1,2,4-thiadiazol)-yl]quinuclidine;
3-[5-(3-dimethylamino-1,2,4-thiadiazol)-yl]quinuclidine;
3-[5-(3-methylmercapto-1,2,4-thiadiazol)-yl]quinuclidine;
3-[5-(3-ethyl-1,2,4-thiadiazol)-yl]quinuclidine;
3-[5-(3-cyclopropyl-1,2,4-thiadiazol)-yl]quinuclidine;
3-[5-(3-dimethylamino-1,2,4-thiadiazol)-yl]-1-azabicyclo[2.2.1]heptane;
3-[5-(3-methoxy-1,2,4-thiadiazol)-yl]quinuclidine;
3-[5-(1,2,4-thiadiazol)-yl]-1-azabicyclo[2.2.1]heptane;
3-[5-(3-cyclopropyl-1,2,4-thiadiazol)-yl]-1-azabicyclo[2.2.1]heptane;
3-[5-(3-benzyl-1,2,4-thiadiazol)-yl]quinuclidine;
3-[5-(3-t-butyl-1,2,4-thiadiazol)-yl]quinuclidine;
5-[5-(3-methyl-1,2,4-thiadiazol)-yl]-1-azabicyclo[2.2.1]heptan-3-ol;
3-[5-(3-isopropyl-1,2,4-thiadiazol)-yl]quinuclidine;
3-[5-(3-ethyl-1,2,4-thiadiazol)-yl]-1-azabicyclo[2.2.1]heptane;
1-methyl-3-[5-(1,2,4-thiadiazol)-yl]-1,2,5,6-tetrahydropyridine;
3-[5-(1,2,4-thiadiazol)-yl]-1,2,5,6-tetrahydropyridine;
1-methyl-3-[5-(3-methyl-1,2,4-thiadiazol)-yl]-1,2,5,6-tetrahydropyridine;
3-[5-(3-methyl-1,2,4-thiadiazol)-yl]-1,2,5,6-tetrahydropyridine;
3-[5-(3-(1-hydroxy-1-phenylmethyl)-1,2,4-thiadiazol)-yl]quinuclidine;
3-[5-(3-benzoyl-1,2,4-thiadiazol)-yl]quinuclidine;
3-[5-(3-(1,1-diphenyl-1-hydroxymethyl)-1,2,4-thiadiazol)-yl]quinuclidine;
6-[5-(3-methyl-1,2,4-thiadiazol)-yl]-1-azabicyclo[3.2.1]octane;
1-methyl-3-[5-(3-dimethylamino-1,2,4-thiadiazol)-yl]-1,2,5,6-tetrahydropyridine;
3-[5-(3-dimethylamino-1,2,4-thiadiazol)-yl]-1,2,5,6-tetrahydropyridine;
1-methyl-3-[5-(3-methylamino-1,2,4-thiadiazol)-yl]-1,2,5,6-tetrahydropyridine;
1-methyl-3-[5-(3-ethylamino-1,2,4-thiadiazol)-yl]-1,2,5,6-tetrahydropyridine;
5-[5-(3-dimethylamino-1,2,4-thiadiazol)-yl]-1-azabicyclo[2.2.1]heptan-3-ol;
3-[5-(3-isopropyl-1,2,4-thiadiazol)-yl]-1-azabicyclo[2.2.1]heptane;
6-[5-(3-cyclopropyl-1,2,4-thiadiazol)-yl]-2-azabicyclo[2.2.2]octane;
3-[5-(3-n-propyl-1,2,4-thiadiazol)-yl]-1-azabicyclo[2.2.1]heptane;
3-[5-(3-methoxy-1,2,4-thiadiazol)-yl]-1-azabicyclo[2.2.1]heptane;
3-[5-(3-methylthio-1,2,4-thiadiazol)-yl]-1-azabicyclo[2.2.1]heptane;
3-[5-(3-n-propyl-1,2,4-thiadiazol)-yl]quinuclidine;
6-[5-(3-isopropyl-1,2,4-thiadiazol)-yl]-2-azabicyclo[2.2.2]octane;
6-[5-(3-ethyl-1,2,4-thiadiazol)-yl]-2-azabicyclo[2.2.2]octane;
5-[5-(3-isopropyl-1,2,4-thiadiazol)-yl]-1-azabicyclo[2.2.1]heptan-3-ol;
3-[5-(3-benzyl-1,2,4-thiadiazol)-yl]-1-azabicyclo[2.2.1]heptane;
1-methyl-3-[5-(3-amino-1,2,4-thiadiazol)-yl]pyrrolidine;
1-methyl-3-[5-(3-amino-1,2,4-thiadiazol)-yl]-1,2,5,6-tetrahydropyridine;
3-[5-(3-amino-1,2,4-thiadiazol)-yl]-1,2,5,6-tetrahydropyridine;
3-[5-(3-amino-1,2,4-thiadiazol)-yl]quinuclidine;
6-[5-(3-methyl-1,2,4-thiadiazol)-yl]-1-azabicyclo[3.2.1]octane;
6-[5-(3-amino-1,2,4-thiadiazol)-yl]-1-azabicyclo[3.2.1]octane;
3-[5-(3-amino-1,2,4-thiadiazol)-yl]-1-azabicyclo[2.2.1]heptane;
5-[5-(3-methyl-1,2,4-thiadiazol)-yl]quinuclidin-3-ol;
5-[5-(3-amino-1,2,4-thiadiazol)-yl]quinuclidin-3-ol;
5-methyl-3-[5-(3-methyl-1,2,4-thiadiazol)-yl]quinuclidine;

5-methyl-3-[5-(3-amino-1,2,4-thiadiazol)-yl]quinuclidine;

5-[5-(3-amino-1,2,4-thiadiazol)-yl]-1-azabicyclo[2.2.1]heptan-3-ol;

3-methyl-3-[5-(3-methyl-1,2,4-thiadiazol)-yl]-1-azabicyclo[2.2.1]heptane;

5-methyl-3-[5-(3-amino-1,2,4-thiadiazol)-yl]-1-azabicyclo[2.2.1]heptane;

3-[5-(3-ethoxy-1,2,4-thiadiazol)-yl]-1-azabicyclo[2.2.1]heptane;

3-[5-(3-chloro-1,2,4-thiadiazol)-yl]-1-azabicyclo[2.2.1]heptane;

3-[5-(3-methylamino-1,2,4-thiadiazol)-yl]-1-azabicyclo[2.2.1]heptane;

3-[5-(3-ethylamino-1,2,4-thiadiazol)-yl]-1-azabicyclo[2.2.1]heptane;

3-[5-(3-ethyl-1,2,4-thiadiazol)-yl]-1,2,5,6-tetrahydropyridine;

3-[5-(3-n-propyl-1,2,4-thiadiazol)-yl]-1,2,5,6-tetrahydropyridine;

3-[5-(3-cyclopropyl-1,2,4-thiadiazol)-yl]-1,2,5,6-tetrahydropyridine;

3-[5-(3-benzyl-1,2,4-thiadiazol)-yl]-1,2,5,6-tetrahydropyridine;

3-[5-(3-methoxy-1,2,4-thiadiazol)-yl]-1,2,5,6-tetrahydropyridine;

3-[5-(3-ethoxy-1,2,4-thiadiazol)-yl]-1,2,5,6-tetrahydropyridine;

3-[5-(3-chloro-1,2,4-thiadiazol)-yl]-1,2,5,6-tetrahydropyridine;

3-[5-(3-methylthio-1,2,4-thiadiazol)-yl]-1,2,5,6-tetrahydropyridine;

3-[5-(3-methylamino-1,2,4-thiadiazol)-yl]-1,2,5,6-tetrahydropyridine;

3-[5-(3-ethylamino-1,2,4-thiadiazol)-yl]-1,2,5,6-tetrahydropyridine;

1-methyl-3-[5-(3-ethyl-1,2,4-thiadiazol)-yl]-1,2,5,6-tetrahydropyridine;

1-methyl-3-[5-(3-n-propyl-1,2,4-thiadiazol)-yl]-1,2,5,6-tetrahydropyridine;

1-methyl-3-[5-(3-cyclopropyl-1,2,4-thiadiazol)-yl]-1,2,5,6-tetrahydropyridine;

1-methyl-3-[5-(3-benzyl-1,2,4-thiadiazol)-yl]-1,2,5,6-tetrahydropyridine;

1-methyl-3-[5-(3-methoxy-1,2,4-thiadiazol)-yl]-1,2,5,6-tetrahydropyridine;

1-methyl-3-[5-(3-methylthio-1,2,4-thiadiazol)-yl]-1,2,5,6-tetrahydropyridine;

1-methyl-3-[5-(3-isopropyl-1,2,4-thiadiazol)-yl]-1,2,5,6-tetrahydropyridine;

3-[5-(3-isopropyl-1,2,4-thiadiazol)-yl]-1,2,5,6-tetrahydropyridine;

5-[5-(3-cyclopropyl-1,2,4-thiadiazol)-yl]-1-azabicyclo[2.2.1]heptan-3-ol;

6-[5-(3-dimethylamino-1,2,4-thiadiazol)-yl]-2-azabicyclo-[2.2.2]octane;

and salts and prodrugs thereof.

Most of the compounds of this invention have at least one asymmetric centre and often more than one; and can therefore exist as both enantiomers and diastereoisomers. In particular, those compounds possessing an unsymmetrical azabicyclic ring system may exist as exo and endo diastereoisomers. It is to be understood that the invention covers all such isomers and mixtures thereof.

Also included within the scope of the present invention are salts of the novel compounds. It will be appreciated that salts of the compounds for use in medicine will be non-toxic pharmaceutically acceptable salts. Other salts may, however, be useful in the preparation of the compounds of the invention or their non-toxic pharmaceutically acceptable salts. Acid addition salts, for example, may be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid or phosphoric acid. Where the novel compound carries a carboxylic acid group the invention also contemplates salts thereof, preferably non-toxic pharmaceutically acceptable salts thereof, such as the sodium, potassium and calcium salts thereof.

Salts of amine groups may also comprise the quaternary ammonium salts in which the amino nitrogen atom carries an alkyl, alkenyl, alkynyl or aralkyl group. Such quaternary ammonium derivatives penetrate poorly into the central nervous system and are therefore useful as peripherally selective muscarinic agents, useful for example as antispasmodic agents, agents to reduce gastric acid secretion, agents to block the muscarinic actions of acetylcholinesterase inhibitors in the treatment of myasthenia gravis and as agents to co-administer with muscarinic agonists in Alzheimer's disease.

It is believed that those compounds of the invention which directly stimulate postsynaptic receptors are particularly useful as analgesic agents.

The method of treatment of this invention includes a method of treating Alzheimer's disease, senile dementia of the Alzheimer type, Huntington's chorea, tardive dyskinesia, hyperkinesia, mania or Tourette syndrome by the administration to a patient in need of such treatment of an effective amount of one or more of the novel compounds.

Moreover, the invention provides in a further aspect a method of treating severe painful conditions (e.g. rheumatism, arthritis and terminal illness) which comprises administering to a patient in need of analgesic treatment an effective amount of one or more of the analgesic compounds according to the invention.

This invention therefore also provides a pharmaceutical composition comprising a compound of the invention and a pharmaceutically acceptable carrier.

It may, where appropriate, be advantageous, in order to reduce unwanted peripherally mediated side-effects, to incorporate into the composition a peripherally acting cholinergic antagonist (or anti-muscarinic agent). Thus the compounds of the invention may advantageously be administered together with a peripheral cholinergic antagonist such as N-methylscopolamine, N-methylatropine, propantheline, methantheline or glycopyrrolate.

The compounds of the invention can be administered orally, parenterally or rectally at a daily dose of about 0.01 to 10 mg/kg of body weight, preferably about 0.1 to 1 mg/kg, and may be administered on a regimen of 1–4 times a day. When a cholinergic antagonist is administered, it is incorporated at its conventional dose.

The pharmaceutical formulations of this invention preferably are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, e.g. conventional tabletting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups and flavoured emulsions with edible oils such as cottonseed oil, sesame oil, coconut oil and peanut oil, as well as elixirs and similar pharmaceutical vehicles. Suitable dispersing or suspending agents for aqueous suspension include synthetic and natural gums such as tragacanth, acacia, alginate, dextran, sodium carboxymethylcellulose, methylcellulose, polyvinyl-pyrrolidone and gelatin.

The 1,2,4-thiadiazoles of formula IA may be prepared by a process which comprises the cyclisation of a compound of formula III:

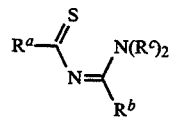
(III)

wherein one of $R^a$ and $R^b$ is a group $R^1$, and the other is a group $R^2$; and $R^c$ is hydrogen or an alkyl group.

Cyclisation of compound III can be achieved using an aminating agent such as hydroxylamine-O-sulphonic acid in a lower alkanol such as methanol, ethanol or propanol, in the presence of pyridine, at between $-20°$ C. and $50°$ C. for about 1–6 hours.

Cyclisation of compounds of formula III ($R^c$=H) may also be achieved by use of an oxidising agent such as bromine, iodine, hydrogen peroxide or nitric acid.

The 1,2,4-thiadiazoles may also be prepared by cycloaddition of a nitrile sulphide $R^a$—C≡N+—S− with a nitrile of formula $R^b$CN where $R^a$ and $R^b$ are as defined above.

A further method for the preparation of the 1,2,4-thiadiazoles of this invention comprises reaction of a thiadiazole of formula IV:

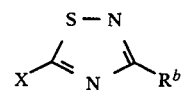
(IV)

with a reagent which provides an anion $-R^a$, where $R^a$ and $R^b$ are as previously defined and X represents halogen. Compound IV may be prepared by the general method described in Chem. Ber., 1957, 90, 182.

Reagents which may provide the anion $-R^a$ include a Grignard reagent $R^a$MgY (where Y=halogen); an organocuprate reagent such as $LiR^a{}_2Cu$; an organolithium reagent $R^a$Li; or a compound which stabilises the anion by means of an adjacent activating group such as an ester or enolisable ketone function. In this case, the adjacent ester or ketone function may be retained after the process is complete, or may be removed. For example, an ester moiety may be hydrolysed and decarboxylated.

1,2,5-Thiadiazoles of this invention may be prepared by reacting a diamine of the type

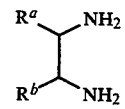

where $R^a$ and $R^b$ are as defined above, with a sulphur chloride such as thionyl chloride or sulphur dichloride.

1,3,4-Thiadiazoles of this invention may be prepared by dehydration of a thiosemicarbazide of formula $R^x$CSNHNHCONR$^p$R$^q$ where $R^x$ is an azacyclic or azabicyclic ring system and $R^p$ and $R^q$ are hydrogen or an alkyl group, with a dehydrating agent such as sulphuric acid, polyphosphoric acid or methanesulphonic acid.

The azacyclic or azabicyclic moiety may be introduced into the molecules concerned by methods known from the art, in particular by methods analogous to those described in EP-A-0239309.

After any of the above described processes is complete, one substituent of low lipophilicity can be converted to another. For example an amino group may be converted to chloro, or hydrazo, —NHNH$_2$, via the intermediacy of diazonium, —N$^2$. Similarly, a chloro substituent may be converted to methoxy by reaction with a nucleophile such as methoxide; and alkoxycarbonyl groups may be converted, via carboxy, to an amino substituent, —NH$_2$.

In any of the above reactions it may be necessary and/or desirable to protect any sensitive groups in the compounds. For example, if $R^a$ and/or $R^b$ include amino, carboxy, hydroxy or thiol groups, these may be protected in conventional manner. Thus, suitable protecting groups for hydroxy groups include silyl groups such as trimethylsilyl or t-butyldimethylsilyl, and etherifying groups such as tetrahydropyranyl; and for amino groups include benzyloxycarbonyl and t-butoxycarbonyl. Carboxy groups are preferably protected in a reduced form such as in the form of their corresponding protected alcohols, which may be subsequently oxidised to give the desired carboxy group. Thiol groups may be protected by disulphide formation, either with the thiol itself or with another thiol to form a mixed disulphide. The protecting groups may be removed at any convenient stage in the synthesis of the desired compound according to conventional techniques.

The following Examples illustrate the preparation of compounds according to the invention. Each of the compounds of the Examples demonstrates an affinity for the muscarinic receptor, having an $IC_{50}$ (concentration required to displace 50% of specific [$^3$H]-N-methylscopolamine binding from rat cortical membrane preparations) significantly lower than 100 μM. Penetrability into the central nervous system of compounds of this invention was assessed by a measurable displacement of radioligand binding using standard "ex-vivo" binding techniques (Ref: *J. Neurosurg.*, 1985, 63, 589–592).

In the Examples, all temperatures are in °C.; THF is tetrahydrofuran; and ether is diethyl ether.

EXAMPLE 1

3-[5-(3-Methyl-1,2,4-thiadiazo)-yl]pyrrolidine Hydrochloride a) 3-Methoxycarbonylpyrrolidine This was prepared by the method described by M. Joucla and J. Mortier (*J. Chem. Soc., Chem. Commun.*, 1985, 1566) from formaldehyde, glycine and methyl acrylate and obtained as a crude oil which was used without further purification.

b) 1-t-Butyloxycarbonyl-3-methoxycarbonyl pyrrolidine

To a solution of 3-methoxycarbonylpyrrolidine (10 g, 0.077 mol) in dichloromethane (50 ml) at 4° C. was added dropwise a solution of di-t-butyl-dicarbonate (16.9 g, 0.077 mol) in dichloromethane (50 ml). The solution was stirred at 20° C. for 16 hours then evaporated under reduced pressure. The residue was purified by chromatography on silica (eluting with methanol/dichloromethane (1:100)) to give the title compound as a colourless oil (12.9 g); $\nu_{max}$ (liquid film) 1740 cm$^{-1}$ (C=O): m/e 230 (M+1)$^+$; δ (360 MHz, CDCl$_3$) 1.46 (9H,s,C(CH$_3$)$_3$, 2.10–2.15 (2H,m,4CH$_2$), 3.00–3.10 (1H,m) with 3.25–3.40 (1H,m) and 3.44–3.68 (3H,m) (2CH$_2$, 3CH and 5CH$_2$) and 3.71 (3H,s,OCH$_3$).

c) 1-t-Butyloxycarbonyl-3-carboxamidopyrrolidine

A solution of 1-t-butyloxycarbonyl-3-methoxycarbonyl-pyrrolidine (8.2 g, 36 mmol) in methanol (20 ml) was stirred with water (20 ml) containing sodium hydroxide (1.7 g, 43.2 mmol) for 15 minutes. The methanol was removed under reduced pressure and the remaining solution acidified with acetic acid and extracted (6×) with dichloromethane. The combined extracts were dried (sodium sulphate) and concentrated in vacuo to give a white solid. This solid was dissolved in dichloromethane (40 ml) containing triethylamine (1.96 g, 19 mmol) and cooled to 0° C. Ethyl chloroformate (2.12 g, 19 mmol) was added and the solution was allowed to warm to 20° C. before bubbling ammonia through until the solution was basic. The reaction mixture was poured onto water and extracted with dichloromethane (6×). The combined extracts were dried with sodium sulphate and concentrated to give the amide (3.7 g) mp 111°–113° C.; $\nu_{max}$ (nujol) 3350, 3175, 1695, 1665 and 1635 cm$^{-1}$; m/e 213 (CI−, [M−1]−); δ (360 MHz, CDCl$_3$) 1.45 (9H, s. (CH$_3$)$_3$), 2.07–2.16 (2H,m,4CH$_2$), 2.88–3.00 and 3.28–3.38 (each 1H, each m, 5CH$_2$), 3.44–3.68 (3H, m, 2CH$_2$ and 3CH) and 5.82–6.04 (2H, bd, NH$_2$).

d) 1-t-Butyloxycarbonyl-3-thiocarboxamidopyrrolidine 1-t-Butyloxycarbonyl-3-carboxamidopyrrolidine (214 mg, 1 mmol) was heated under reflux in benzene (10 ml) with Lawesson's reagent (202 mg, 0.5 mmol) for 2 hours. The mixture was cooled then chromatographed on silica gel eluting with methanol/dichloromethane (1:20) to give the thioamide (103 mg), as a solid, mp 131°–133° C.; $\nu_{max}$ (nujol) 3300, 3180, 1670, 1650, 1165, and 1130 cm$^{-1}$; m/e 229 (CI−, [M−1]−); δ (360MH$_2$, CDCl$_3$) 1.44 (9H, s, (CH$_3$)$_3$), 2.14–2.22 (2H, m, 4CH$_2$), 3.27–3.37 (2H, m, 5CH$_2$), 3.54–3.70 (3H, m, 2CH$_2$ and 3CH) and 8.06–8.20 (2H, bs, NH$_2$).

e) 1-t-Butyloxycarbonyl-3-(N,N-dimethylacetamidinothiocarbonyl)pyrrolidine 1-t-Butyloxycarbonyl-3-thiocarboxamidopyrrolidine (230 mg, 1 mmol) in dichloromethane (10 ml) was treated with dimethylacetamide dimethylacetal (287 mg, 2.4 mmol) for 16 hours. The mixture was chromatographed on silica eluting with methanol/dichloromethane (1:20) to give the title compound as an oil (320 mg); m/e 300 (CI+, [M+1]+); δ (360 MHz, CDCl$_3$) 1.45 (9H,s,C(CH$_3$)$_3$), 2.13–2.27(2H, m, 4CH$_2$), 2.42 and 2.43 (3H, 2×s, N=CCH$_3$ E and Z isomers), 3.10 and 3.12 (3H, 2×s) and 3.20 and 3.21 (3H, 2×s, (N(CH$_3$)$_2$), 3.25–3.36 (1H, m) and 3.42–3.66 (4H, m) (2CH$_2$, 3CH and 5CH$_2$).

f) 3-[5(3-Methyl-1,2,4-thiadiazol)-yl]pyrrolidine Hydrochloride

The thioacylamidine prepared as in (e) (2.8 g, 9.4 mmol) in ethanol (50 ml) was treated with pyridine (1.5 g, 18.8 mmol) and hydroxylamine-O-sulphonic acid (1.3 g, 11.2 mmol) in methanol (10 ml) for 2 hours. The solvents were removed in vacuo and the residue taken up in water and dichloromethane. The dichloromethane was separated, dried with sodium sulphate and concentrated in vacuo. The residue was dissolved in ethanol (50 ml) and 2N HCl (20 ml) and heated under reflux for 20 minutes. The ethanol was removed in vacuo and water (10 ml) was added and extracted with dichloromethane. The aqueous solution was adjusted to pH10 with sodium carbonate and extracted four times with dichloromethane. The combined extracts were dried and concentrated under reduced pressure and the residue, in diethyl ether, treated with ethereal hydrogen chloride. The resulting gum was triturated with diethyl ether to give the title compound as a white solid (670 mg), mp 135°–137° C.; (Found: C, 38.2: H, 5.5; N,18.9. C$_7$H$_{11}$N$_3$S. HCl requires C, 38.2; H, 5.7; N, 19.1%); m/e 170 (CI+,[M+1]+); δ (360 MHz, D$_2$O) 2.25–3.39 (1H,m) and 2.63–2.70 (1H,m, (4CH$_2$), 2.62 (3H, s, CH$_3$), 3.47–3.64 (3H, m, one of 2CH$_2$, and 5CH$_2$), 3.85 (1H, dd, J=7 Hz and 9.5 Hz, one of 2CH$_2$) and 4.24 (1H, quin, J=7 Hz).

EXAMPLE 2

1-Methyl-3-[5-(3-methyl-1,2,4-thiadiazol)-yl ]pyrrolidine Hydrogen Oxalate

A solution of 3-[5-(3-methyl-1,2,4-thiadiazol)-yl]-pyrrolidine in formic acid (3 ml) containing formaldehyde (3 ml of a 40% solution in water) was heated under reflux for 15 minutes. The mixture was evaporated to dryness under reduced pressure and the residue partitioned between aqueous potassium carbonate solution and dichloromethane. The dichloromethane portion was separated, dried and concentrated in vacuo. The residue was purified by chromatography on silica gel eluting with methanol/dichloromethane (1:10) and the product thus obtained treated with oxalic acid. The precipitated salt was triturated with diethyl ether leaving the title compound as a white solid (125 mg), mp 105°–107° C.; (Found: C, 43.2; H, 5.2; N, 15.0. C$_8$H$_{13}$N$_3$S (COOH)$_2$.0.25H$_2$O requires C,43.2; H, 5.6; N, 15.1%); m/e 184 (CI+, [M+1]+); δ (360 MHz, D$_2$O) shows two isomers in ratio 1:1, 2.28–2.39, 2.44–2.50, 2.65–2.72 and 2.79–2.84 (each 0.5H, each m, 4CH$_2$) 2.61 and 2.62 (each 1.5H, each s, CCH$_3$), 3.03 and 3.05 (each 1.5H, each s, NCH$_3$), 3.29–3.46 (1.5H, m) with 3.65 (0.5H, dd, J=9 Hz and 12 Hz), 3.83–3.98(1.5H, m) and 4.18(0.5H, dd, J=7.5 Hz and 12 Hz) (2CH$_2$ and 5CH$_2$), 4.28(0.5H, quin, J=8.5 Hz, 0.5(3CH)) and 4.44 (0.5H, quin, J=7 Hz, 0.5(3CH)).

EXAMPLE 3

3-[5(3-Methyl-1,2,4-thiadiazol)-yl]quinuclidine Hydrogen Oxalate a) 3-[5-(3-Methyl-1,2,4-thiadiazol)-yl]-3-methoxycarbonyl-quinuclidine Hydrochloride 3-Methoxycarbonylquinuclidine (7.2 g, 42 mmol), prepared by the method of C. A. Grob and E. Renk (*Helv. Chim. Acta.*, (1954), 37, 1689), was dissolved in tetrahydrofuran (400 ml) at −78° C. under an atmosphere of nitrogen. Lithium diisopropylamide. THF (40 ml of a 1.5M solution in cyclohexane, 60 mmol) was added slowly and the reaction was stirred at −78° C. for 1 hour. 5-Chloro-3-methylthiadiazole (7.0 g, 52 mmol), prepared by the method of J. Goerdeler et al, *Chem. Ber.*, (1957), 90, 182, was added and the mixture was allowed to warm slowly to room temperature over 2 hours. The solvent was removed under reduced pressure and dilute hydrochloric acid was added to the residue. The aqueous solution was extracted twice with diethyl ether then made basic with potassium carbonate. The aqueous solution was again extracted three times and these extracts were dried with sodium sulphate and then treated with dry hydrogen chloride in diethyl ether. The precipitated salt was recrystallised from methanol-ethyl acetate to give the title compound (1.52 g), mp 142° C.; (Found: C, 47.55; H, 5.96; N, 13.76. C$_{12}$H$_{18}$N$_3$O$_2$S. HCl requires C, 47.28; H, 6.28; N, 13.78%). ν$_{max}$ (dichloromethane) 2260 (N—H), 1750 cm$^{-1}$ (C=O); m/e 267 (M+ of free base); δ (360 MHz, D$_2$O) 1.74–1.85 (1H, m) and 1.91–2.14 (3H, m) (5CH$_2$ and 8CH$_2$), 2.65 (3H,s, CCH$_3$), 2.90–2.92 (1H,m,4CH), 3.28–3.46 (4H,m, 6CH$_2$ and 7CH$_2$), 3.92 (3H, s, OCH$_3$), 4.27 (1H,d, J=14 Hz, one of 2CH$_2$) and 4.43 (1H, dd, J=14 Hz and 2.5 Hz, one of 2CH$_2$).

b) 3-[5-(3-Methyl-1,2,4-thiadiazol)-yl]quinuclidine Hydrogen Oxalate

3-[5-(3-Methyl-1,2,4-thiadiazol)-yl]-3-methoxycarbonyl-quinuclidine hydrochloride (300 mg, 0.97 mmol) in tetrahydrofuran (7 ml) was treated with 1N aqueous sodium hydroxide (2.2 ml) for 2 hours. The tetrahydrofuran was evaporated off under reduced pressure and the aqueous solution adjusted to pH 2 with concentrated hydrochloric acid. After 15 minutes the solution was made basic with potassium carbonate and extracted with dichloromethane which was then dried with sodium sulphate and concentrated in vacuo. The residue dissolved in diethyl ether was treated with oxalic acid in diethyl ether and the resulting salt recrystallised from methanol/diethyl ether to give the title compound (260 mg), mp 159°–160° C. (Found: C, 45.51; H, 5.31; N, 12.27; C$_{10}$H$_{15}$N$_3$S. 1.5(COOH)$_2$ requires C, 45.34; H, 5.27; N, 12.20%); m/e 210 (CI+, [M+1]+ of free base); δ (360 MHz, D$_2$O) 1.88–1.94 and 2.07–2.16 (each 2H, each m, 5CH$_2$ and 8CH$_2$), 2.50–2.55 (1H, m, 4CH), 2.63 (3H, s, CH$_3$), 3.30–3.52 (4H, m, 6CH$_2$ and 7CH$_2$), 3.78(1H, dd, J=7 Hz and 14Hz, one of 2CH$_2$), 3.86 (1H, t, J=14 Hz, one of 2CH$_2$) and 4.06–4.13(1H, m, 3CH).

EXAMPLE 4

3-[5-(3-Methyl-1,2,4-thiadiazol)-yl]-1-azabicyclo[2,2,1]-heptane H]Hydrogen Oxalate a) 1-Benzyl-3-ethoxycarbonylpyrrolidine A solution of 1-benzyl-3-hydroxymethylpyrrolidine (60 g, 0.314 mol: *J. Org. Chem.*, (1961), 26, 1519) in conc. sulphuric acid (7.3 ml) and water (350 ml) was treated at 0° C. with a solution of chromium trioxide (26.2 g) in conc. sulphuric acid (18 ml) and water (410 ml). The mixture was stirred at 0° C. for 5 min, 100° C. for 2 min and then cooled back to 0° C. A further charge of the chromium trioxide solution was then added and the mixture heated at 100° C. for 0.5 h. After cooling again to 10° C., excess sodium metabisulphite was added to destroy any remaining oxidant and the pH adjusted to 10 with 6N-sodium hydroxide solution. After filtration, the mixture was acidified to pH 2 with 6N-hydrochloric acid and the solution evaporated. The rigorously dried residue was treated at 20° C. for 16 h with anhydrous ethanol saturated with hydrogen chloride. The gum after evaporation of the solvent was partitioned between dichloromethane and water made basic with excess potassium carbonate and the required ethyl ester isolated from the organic layer (25 g); δ (60 MHz, CDCl$_3$) 1.20 (3H, t, J=6.5 Hz, CH$_3$); 1.9–2.2 (5H, m, 2×CH$_2$ and CH); 3.60 (2H, s, CH$_2$ Ph); 4.10 (2H, q, J=6.5 Hz, CH$_2$ CH$_3$) and 7.23 (5H, broad s, C$_6$H$_5$).

b) 1-Ethoxycarbonylmethyl-3-ethoxycarbonylpyrrolidine

The foregoing 1-benzylpyrrolidine (18 g) in ethanol (400 ml) was subjected to hydrogenolysis over Pd(OH)$_2$ (5 g) at 50 psi in a Paar shaker for 72 h. After filtration, the solvent was evaporated and the resulting oil purified by chromatography on alumina in methanol-dichloromethane (1:19) to give 3-ethoxycarbonyl-pyrrolidine (8 g) as a colourless oil. This amine (7.75 g, 54 mmol) in ether (70 ml) was treated at 0° C. with a solution of ethyl bromoacetate (4.53 g, 27 mmol) in ether (40 ml) in the presence of solid potassium carbonate (5 g). After 0.5 h at 0° C. and 1 h at reflux, the precipitated solid was removed by filtration and the residue isolated from the filtrate purified by chromatography on alumina in dichloromethane to give the diester (5.56 g); δ (60 MHz, CDCl$_3$) 1.25 (6H, t, J=7 Hz, 2×CH$_3$); 2.1–3.2 (7H, m, 3×CH$_2$ and CHCO); 3.3 (2H, s, CH$_2$CO) and 4.15 and 4.20 (each 2H, each q, each J =7 Hz, 2×OCH$_2$).

c) 1-Azabicyclo[2,2,1]heptan-3-one

A mixture of ethanol (4.5 ml) and toluene (6 ml) was added dropwise to a rapidly stirred suspension of potassium (2.66 g, 68.2 mmol) in toluene (15 ml) at 120° C. under nitrogen. After 1 h at this temperature, a solution of the foregoing diester (6.24 g, 27.3 mmol) in toluene (25 ml) was then added and the mixture heated at 140° C. for 3 h. Concentrated hydrochloric acid (90 ml) was added, the two solvent phases separated and the aqueous phase heated under reflux for 18 h. The reaction mixture was evaporated to half volume, neutralised with solid potassium carbonate and extracted with dichloromethane. The material isolated from the organic extracts was chromatographed on silica in methanol-dichloromethane (1:9) to give the required azabicycle (250 mg), δ (CDCl$_3$, 360 MHz) 1.75–1.80 (1H, m, H of CH$_2$); 2.06–2.12 (1H, m, H of CH$_2$); 2.70–2.81 (4H, m, 2×NCH$_2$) and 3.00–3.12 (3H, m, COOH$_2$ and CH).

d) 3-(1,3-Dithian-2-ylidene)-1-azabicyclo[2,2,1]heptane

A solution of n-butyl lithium in hexane (1.4 ml of a 1.6M solution: 2.3 mmol) was added to a solution of 2-trimethylsilyl-1,3-dithiane (457 mg, 2.37 mmol) in tetrahydrofuran (5 ml) stirred under nitrogen at −35° C. After 1.5 h, the foregoing ketone (220 mg, 1.98 mmol) in tetrahydrofuran (5 ml) was added and the mixture allowed to warm to 20° over 1 h. Water (20 ml) was added and the solution extracted with dichloromethane. Chromatography of the material isolated from the organic extracts on alumina in methanol-dichloromethane (1:49) gave the dithioacetal ketene (370 mg), δ (CDCl$_3$, 360 MHz) 1.35–1.48 (1H, m, CH); 1.76–1.90 (2H, m, CH$_2$); 2.10–2.17 (2H, m, CH$_2$); 2.43 (1H, dd, J=3 Hz and 9 Hz, bridge CH); 2.46–2.58 (1H, m, CH); 2.62 (1H, m, CHN); 2.70–2.94 (5H, m, CH and 2×CH$_2$S); 3.02 (1H, dd, J=3 Hz and 18 Hz. CH—C=C) and 3.41 (1H, dd, J=3 Hz and 18 Hz, CH—C=C).

e) 3-Methoxycarbonyl-1-azabicyclo-[2,2,1]-heptane

The foregoing ketene dithioacetal (3.4 g) in dry methanol (100 ml) saturated with anhydrous hydrogen chloride was stirred at 55° C. for 12 hours. After evaporation of the solvent, the residue was dissolved in water which was washed (6×) with diethyl ether. The aqueous solution was adjusted to pH 10 with potassium carbonate and extracted (3×) with dichloromethane. The combined extracts were dried and concentrated in vacuo to give the title compound (1.56 g) as an oil: δ (360 MHz, CDCl$_3$) 1.12–1.19 (1H, m, one of 5CH$_2$), 1.56–1.65 (1H, m, one of 5CH$_2$), 2.21–2.25 (1H, m) with 2.32–2.35 (1H, m), 2.40–2.50 (1H, m), 2.62–2.66 (1H, m), 2.73–2.87 (3H, m) and 2.96–3.01 (1H, m) (2CH$_2$, 3CH, 4CH, 6CH$_2$ and 7 CH$_2$), and 3.67 (3H, s, OCH$_3$).

f) 3-[5-(3-Methyl-1,2,4-thiadiazol)-yl]-1-azabicyclo-[2,2,1]-heptane Hydrogen Oxalate To a solution of 3-methoxycarbonyl-1-azabicyclo-[2,2,1]-heptane (1.55 g, 10 mmol) in tetrahydrofuran (40 ml) at −78° C. under an atmosphere of nitrogen was added lithium diisopropylamide. THF complex (8.6 ml of a 1.5M solution in cyclohexane, 12.9 mmol). The solution was stirred at −78° C. for 1 hour then 3-methyl-5-chloro-1,2,4-thiadiazole was added after which the temperature was maintained at −78° C. for 1 hour then allowed to warm slowly to room temperature. The solvent was removed in vacuo, then aqueous potassium carbonate was added and extracted (4×) with dichloromethane. The combined extracts were dried and concentrated, and the residue dissolved in methanol (50 ml). 2N sodium hydroxide solution (50 ml) was added and the mixture stirred for 0.75 hours, then the methanol was evaporated under reduced pressure. The aqueous solution was washed (3×) with dichloromethane then adjusted to pH2 with concentrated hydrochloric acid. After 10 minutes the solution was made basic with potassium carbonate and extracted (3×) with dichloromethane. The combined extracts were dried and concentrated and the residue chromatographed on alumina. Elution with a gradient going from neat ethyl acetate to 5% methanol/ethyl acetate gave first, the minor isomer of the title compound free base, converted to the oxalic acid salt in ether and recrystallised from methanol/diethyl ether (15 mg), mp 163°–4° C. δ (360 MHz, D$_2$O) 1.98–2.06 (1H, m, one of 5CH$_2$), 2.22–2.32 (1H, m, one of 5CH$_2$), 2.61 (3H, s, CH$_3$), 3.25–3.30 (2H, m) with 3.34–3.42 (1H, m), 3.51–3.58 (2H, m), 3.82 (2H, m), and 3.98 (1H, m), (2CH$_2$, 3CH, 4CH, 6CH$_2$ and 7CH$_2$); m/e.

Further elution gave the second product which was treated with oxalic acid and recrystallised from methanol/diethyl ether to give the major isomer of the title compound (90 mg), mp 143°–4° C. (Found: C, 46.21; H, 5.35; N, 14.49. C$_9$H$_{13}$N$_3$S.(COOH)$_2$ requires C, 46.31; H, 5.30; N, 14.73%). m/e 195 (M$^+$ of free base); δ (360 MHz, D$_2$O) 1.64–1.74 (1H, m, one of 5CH$_2$), 2.00–2.10 (1H, m, one of 5CH$_2$), 2.64 (3H, s, CH$_3$), 3.32–3.46 (3H, m) with 3.50–3.58 (2H, m), 3.66 (1H, ddd, J=2.2, 5.7 Hz, and 12.2 Hz), 3.97 (1H, dt, J=3.0 Hz and 11.5 Hz) and 4.35–4.42 (1H, m) (2CH$_2$, 3CH, 4CH, 6CH$_2$ and 7CH$_2$).

EXAMPLE 5

3-[5-(3-Phenyl-1,2,4-thiadiazol)-yl]quinuclidine Hydrochloride

A solution of 3-methoxycarbonyl quinuclidine (940 mg, 5.56 mmol) in tetrahydrofuran (75 ml) was treated with a 1.5M solution of lithium diisopropylamide-tetrahydrofuran complex in cyclohexane (5 ml, 7.5 mmol) at −78° C. under an atmosphere of nitrogen for 1 hour. 5-Chloro-3-phenyl-1,2,4-thiadiazole (1.5 g, 7.7 mmol, prepared by the method of *Chem. Ber.*, (1957), 90, 182) was added and the reaction was allowed to warm slowly to room temperature. The solvent was evaporated under reduced pressure and the residue stirred in methanol (30 ml) and 2N NaOH (20 ml) for 1 hour. The methanol was removed in vacuo and the aqueous solution extracted with ethyl acetate (3×20 ml) then adjusted to pH 2 with concentrated hydrochloric acid. After three hours the solution was made basic and extracted with dichloromethane (3×40 ml). The combined dichloromethane solutions were dried with sodium sulphate and concentrated under reduced pressure to give the title compound free base (210 mg) which was treated with ethereal hydrogen chloride. The resulting salt was recrystallised from dichloromethane-diethyl ether to give the title compound (187 mg), mp 213° C. (decomp.); (Found: C, 56.76; H, 5.84; N, 13.18. C$_{15}$H$_{17}$N$_3$S. HCl. 0.5H$_2$O requires C, 56.86; H, 6.04; N, 13.26%); m/e 271 (M$^+$ of free base); δ (360 MHz, D$_2$O) 1.88–2.06 and 2.13–2.32 (each 2H, each m, 5CH$_2$ and 8CH$_2$), 2.56–2.62 (1H, m, 4CH), 3.36–3.60 (4H, m, 6CH$_2$ and 7CH$_2$), 3.89 (1H, ddd, J=2.5, 10.5 and 13.0 Hz, one of 2CH$_2$), 4.01 (1H, dd, J=6.2 and 13.0 Hz, one of 2CH$_2$), 4.12–4.22 (1H, m, 3CH), 7.6 –7.65 and 8.20–8.26 (3H and 2H respectively, each m, Ph).

EXAMPLES 6–10

The free bases of Examples 6–10 were prepared by the method of Example 5 using the appropriate 5-chloro-1,2,4-thiadiazole.

EXAMPLE 6

3-[5-(1,2,4-Thiadiazol)-yl]quinuclidine Sesqui-Hydrogen Oxalate

3-Methoxycarbonyl quinuclidine (1.25 g, 7.4 mmol) and 5-chloro-1,2,4-thiadiazole (830 mg, 6.9 mmol, prepared by the method of *Chem. Ber.*, (1956), 89, 1534) gave the title compound free base which was treated with oxalic acid. Crystallisation from methanol-diethyl ether gave the title compound (526 mg). mp 131°–2° C.; (Found: C, 43.62; H, 4.89; N, 17.78. C$_9$H$_{13}$N$_3$S. 1.5 (COOH)$_2$ requires C, 43.63H, 4.88; N, 12.72%); m/e 195 (M$^+$ of free base); δ (360 MHz, D$_2$O) 1.84–1.92 and 2.08–2.28 (each 2H, each m, 5CH$_2$ and 8CH$_2$), 2.51–2.56 (1H, m, 4CH), 3.30–3.50 (4H, m, 6CH$_2$ and 7CH$_2$), 3.87 (2H, d, J=8.4 Hz, 2CH$_2$), 4.18 (1H, dt, J=2.4 and 8.4 Hz, 3CH) and 8.74 (1H, s, thiadiazole-H).

EXAMPLE 7

3-[5-(3-Dimethylamino-1,2,4-thiadiazol)-yl]quinuclidine Hydrochloride

3-Methoxycarbonyl quinuclidine (2.40 g, 14.2 mmol) and 5-chloro-3-dimethylamino-1,2,4-thiadiazole (3.0 g, 18 mmol, made by the general method of *Chem. Ber.*, (1957), 90, 188) gave the title compound free base which was treated with ethereal hydrogen chloride. The salt was crystallised from methanol-diethyl ether to give the title compound (130 mg), mp 153°–156° C.; (Found: C, 40.55; H, 6.53; N, 17.13. C$_{11}$H$_{18}$N$_4$S. 2HCl. 0.75H$_2$O requires C, 40.68; H, 6.67; N, 17.25%); m/e 238 (M+ of free base); δ (360 MHz, D$_2$O) 1.82–2.00 and 2.06–2.24 (each 2H, each m, 5CH$_2$ and 8CH$_2$), 2.45–2.50 (1H, m, 4CH), 3.15 (6H, s, 2×CH$_3$), 3.39–3.50 (4H, m, 6CH$_2$ and 7CH$_2$) and 3.74–3.98 (3H, m, 2CH$_2$ and 3CH).

EXAMPLE 8

3-[5-(3-Methylmercapto-1,2,4-thiadiazol)-yl]-quinuclidine Hydrochloride

3-Methoxycarbonyl quinuclidine (2.2 g, 13.0 mmol) with 5-chloro-3-methylmercapto-1,2,4-thiadiazole (3.3 g, 19.5 mmol, prepared by the method of *Chem. Ber.*, (1957), 90, 892) gave the title compound free base which was treated with ethereal hydrogen chloride. Crystallisation from dichloromethanediethyl ether afforded the title compound (280 mg), mp 194°–195° C.; (Found: C, 43.02; H, 5.79; N, 14.83. C$_{10}$H$_{15}$N$_3$S$_2$. HCl requires C, 43.23; H, 5.80; N, 15.12%); m/e 241 (M+ of free base); δ (360 MHz, D$_2$O) 1.88–1.95 and 2.09–2.27 (each 2H, each m, 5CH$_2$ and 8CH$_2$), 2.50–2.56 (1H, m, 4CH), 2.70 (3H, m, CH$_3$), 3.31–3.50 (4H, m, 6CH$_2$ and 7CH$_2$), 3.81–3.86 (2H, m, 2CH$_2$) and 4.08–4.14 (1H, m, 3CH).

EXAMPLE 9

3-[5-(3-Ethyl-1,2,4-thiadiazol)-yl]quinuclidine Hydrochloride

3-Methoxycarbonyl quinuclidine (1.6 g, 9.4 mmol) with 5-chloro-3-ethyl-1,2,4-thiadiazole (1.4 g, 9.4 g, prepared by the method of *Chem. Ber.*, (1957), 90, 182) gave the title compound free base which was treated with ethereal hydrogen chloride. Crystallisation from dichloromethane-diethyl ether afforded the title compound (320 mg), mp 174°–5° C.; (Found: C, 50.34; H, 6.88; N, 15.92. C$_{11}$H$_{17}$N$_3$S. HCl. 0.2H$_2$O requires C, 50.16; H, 7.04; N, 15.95%); m/e 223 (M+ of free base); δ (360 MHz, D$_2$O) 1.34 (3H, t, J=7.5 Hz, CH$_3$), 1.90–1.96 and 2.09–2.29 (each 2H, each m, 5CH$_2$ and 8CH$_2$), 2.53–2.58 (1H, m, 4CH), 3.00 (2H q, J=7.5 Hz, CH$_2$CH$_3$), 3.32–3.50 (4H, m, 6CH$_2$ and 7CH$_2$), 3.81 (1H, ddd, J=2.0, 7.1 and 13.2 Hz, one of 2CH$_2$), 3.89 (1H, ddd, J=2.4, 10.2 and 13.2 Hz, one of 2CH$_2$) and 4.08–4.14 (1H, m, 3CH).

EXAMPLE 10

3-[5-(3-Cyclopropyl-1,2,4-thiadiazol)-yl]-quinuclidine Hydrogen Oxalate

3-Methoxycarbonyl quinuclidine (2.0 g, 11.8 mmol) and 5-chloro-3-cyclopropyl-1,2,4-thiadiazole (2.5 g, 15.4 mmol, prepared by the general method described in *Chem. Ber.*, (1957), 90, 182) gave the title compound free base which was treated with oxalic acid in ether. Crystallisation from methanol-diethyl ether afforded the title compound (540 mg), mp 175°–6° C.; m/e 235 (M+ of free base); δ (360 MHz, D$_2$O) 1.02–1.14 (4H, m, 2×cyclopropyl CH$_2$), 1.84–1.92 and 2.05–2.14 (each 2H, each m, 5CH$_2$ and 8CH$_2$), 2.29–2.38 (1H, m, cyclopropyl CH), 2.46–2.52 (1H, m, 4CH), 3.29–3.49 (4H, m, 6CH$_2$ and 7CH$_2$), 3.81 (2H, d, J=8.7 Hz, 2CH$_2$) and 4.04 (1H, dt, J=2 and 8.7 Hz, 3CH).

EXAMPLE 11 exo- and endo-3-[5-(3-Dimethylamino-1,2,4-thiadiazol)-yl]-1-azabicyclo[2.2.1]heptane a) 1-Carbomethoxymethylene-4-carbomethoxy pyrrolidin-2-one To a solution of glycine methyl ester hydrochloride (476 g, 3.79 mol) in methanol (900 ml) was added sodium methoxide (205 g, 3.79 mol) and dimethyl itaconate (500 g, 3.16 mol) and the mixture was heated under reflux for 16 hours. The reaction was filtered and the solvent removed under reduced pressure. 5N hydrochloric acid (500 ml) was added to the residue which was then extracted with dichloromethane (3×500 ml). The combined extracts were dried with sodium sulphate and evaporated in vacuo to give a residue which was distilled to give the title compound (337 g), bp. 132°–135° C. at 1 mmHg; m/e CI+ 216 [(M+1)+ of free base] δ (360 MHz, CDCl$_3$) 2.68 (1H, dd, J=9.6 and 17.2 Hz, one of 3CH$_2$), 2.75 (1H, dd, J=7.5 and 17.2 Hz, one of 3CH$_2$), 3.30–3.40 (1H, m, 4CH), 3.69–3.78 (2H, m, 5CH$_2$), 3.71 (3H, s, OCH$_3$), 3.74 (3H, s, OCH$_3$), 3.99 (1H, d, J=17.6 Hz, one of NCH$_2$CO$_2$) and 4.16 (1H, d, J=17.6 Hz, one of NCH$_2$CO$_2$).

b) 1-Carbomethoxymethylene-3-carbomethoxy pyrrolidine

The foregoing amide (86 g, 0.4 mol) in THF (500 ml) was added slowly to a 1M solution of BH$_3$. THF (800 ml, 0.8 mol) under nitrogen with cooling from an ice bath. When addition was complete the reaction was heated under reflux for 1 hour then allowed to cool. A saturated aqueous potassium carbonate solution was added and the mixture refluxed for 1 hour, then cooled. The solution was decanted from the precipitated solid and concentrated in vacuo to give a residue which was treated with 5N hydrochloric acid and washed with dichloromethane. The aqueous solution was basified with aqueous potassium carbonate and extracted three times with dichloromethane. The combined extracts were dried (Na$_2$SO$_4$), concentrated, and purified by acetate, to give the title compound (30 g) as a yellow oil, δ (360 MHz, CDCl$_3$) 2.11–2.18 (2H, m, 4CH$_2$), 2.56–2.63 with 2.71–2.78 and 2.88–2.94 (each 1H, each m, 3CH and 5CH$_2$), 3.06–3.15 (2H, m, 2CH$_2$), 3.33 (1H, d, J=16.9 Hz, one of NCH$_2$CO$_2$), 3.39 (1H, d, J=16.9 Hz, one of NCH$_2$CO$_2$), 3.69 (3H, s, OCH$_3$) and 3.73 (3H, s, OCH$_3$).

c) 1-Azabicyclo[2.2.1]heptan-3-one

The foregoing diester (28 g, 0.14 mol) in dry toluene (300 ml) was added over 3 hours to a refluxing solution of potassium tert-butoxide (43 g) in toluene (1.31 t) with vigorous stirring. After complete chromatography on silica gel, eluting with ethyl addition heating was continued for 2 hours then, after cooling, concentrated hydrochloric acid (500 ml) was added. The toluene was decanted off and the acid solution heated to reflux for 15 hours then cooled and concentrated in vacuo. Potassium carbonate solution was added to the residue which was then extracted several times with dichloromethane. The combined extracts were dried and concentrated in vacuo. Diethyl ether was added to the residue and the solution filtered and evaporated to give the title compound (7.2 g) also described in Example 4c.

d) 3-Methoxycarbonyl-1-azabicyclo-[2.2.1]-heptane

This was prepared from the foregoing ketone by the method of Example 4d and 4c.

e) endo-3-[5-(3-Dimethylamino-1,2,4-thiadiazol)-yl]-1-azabicyclo[2.2.1]heptane Hydrogen Oxalate The foregoing ester (1.8 g, 11.6 mmol) in tetrahydrofuran (30 ml) was treated with lithium diisopropylamide-tetrahydrofuran complex (10 ml of a 1.5M solution in cyclohexane, 15 mmol) for 1 hour at −78° C. under an atmosphere of nitrogen. 5-Chloro-3-dimethylamino-1,2,4-thiadiazole (2.5 g, 15.1 mmol) was added as a solution in tetrahydrofuran (20 ml) and the reaction was allowed to warm slowly to room temperature. The solvent was removed under reduced pressure and the residue stirred in methanol (30 ml) and 2N NaOH (25 ml) for 1 hour. The methanol was evaporated under reduced pressure and the aqueous solution washed 3× with ethyl acetate then adjusted to pH2 with concentrated hydrochloric acid and left to stand for 24 hours. The solution was treated with aqueous potassium carbonate until basic and extracted (3×) with dichloromethane. The combined extracts were dried ($Na_2SO_4$) and concentrated in vacuo to give a residue which was treated with oxalic acid in methanol. Crystallisation from methanol-propan-2-ol gave endo-3-[5-(3-dimethylamino-1,2,4-thiadiazol)-yl]-1-azabicyclo[2.2.1]heptane (317 mg), mp 134°-136° C.; (Found: C, 45.76; H, 5.70; N, 17.70. $C_{10}H_{16}N_4S \cdot (COOH)_2$ requires C, 45.85; H, 5.70; N, 17.82%); m/e 224 (M+ of free base); δ (360 MHz, $D_2O$) 1.70-1.79 and 1.97-2.08 (each 1H, each m, $5CH_2$), 3.14 (6H, s, $NMe_2$), 3.33-3.41 and 3.46-3.55 (3H and 2H respectively, each m, 4CH, $6CH_2$ and $7CH_2$), 3.67 (1H, ddd, J=2.3, 5.6 and 12.1 Hz, one of $2CH_2$), 3.88 (1H, dt, J=12.1 and 2.9 Hz, one of $2CH_2$) and 4.20-4.27 (1H, m, 3CH).

f) exo-3-[5-(3-Dimethylamino-1,2,4-thiadiazol)-yl]-1-azabicyclo[2.2.1]heptane Dihydrochloride The mother liquor from the crystallisation above was treated with sodium methoxide in methanol until strongly basic and left to stand for 1 hour. The Solvent was removed and the residue chromatographed on grade III neutral alumina eluting with 0.2% methanol in dichloromethane. Fractions containing the pure faster eluting isomer were combined and evaporated to give exo-3-[5-(3-dimethylamino-1,2,4-thiadiazol)-yl]-1-azabicyclo[2.2.1]heptane (70 mg) which was crystallised as the dihydrochloride salt, mp 155°-156° C. (methanol-diethyl ether); (Found: C, 39.19; H, 6.06; N, 17.86. $C_{10}H_{16}N_4S \cdot 2HCl \cdot 0.6H_2O$ requires C, 38.99; H, 6.28; N, 18.19%); m/e 224 (M+ of free base); δ (360 MHz, $D_2O$) 1.94-2.01 and 2.19-2.29 (each 1H, each m, $5CH_2$), 3.13 (6H, s, $NMe_2$), 3.20 (1H, d, J=4.0 Hz, 4CH), 3.26 (1H, d, J=9.4 Hz, one of $7CH_2$), 3.33-3.40 (1H, m, one of $6CH_2$), 3.43-3.55 (1H, m, one of $6CH_2$), 3.59 (1H, d, J=9.4 Hz, one of $7CH_2$) and 3.74-3.87 (3H, m, 3CH and $2CH_2$).

EXAMPLE 12

3-[5-(3-Methoxy-1,2,4-thiadiazol)-yl]quinuclidine Hydrogen Oxalate

The title compound free base was prepared from 3-methoxycarbonyl quinuclidine and 5-chloro-3-methoxy-1,2,4-thiadiazole (made by the general method of Chem. Ber. (1957), 90, 892 using perchloromethyl mercaptan and O-methylisourea hydrogen sulphate and having b.p. 86°-87° C. (20 mmHg)) using the method described in Example 5. The hydrogen oxalate salt was obtained as a gum, (Found: M+ =225.0922. $C_{10}H_{15}N_3OS$ (free base) requires M+ =225.09358); δ (250 MHz, $D_2O$) 1.84-2.00 and 2.05-2.24 (each 2H, each m, $5CH_2$ and $8CH_2$), 2.42-2.50 (1H, m, 4CH), 3.28-3.50 (4H, m, $6CH_2$ and $7CH_2$), 3.70-3.84 (2H, m, $2CH_2$), 3.96-4.06 (1H, m, 3CH) and 4.09 (3H, s, $CH_3$).

EXAMPLE 13 exo- and endo-3-[5-(1,2,4-Thiadiazol)-yl]-1-azabicyclo[2.2.1]heptane Hydrogen Oxalate To a solution of 3-methoxycarbonyl-1-azabicyclo[2.2.1]heptane (1.05 g, 6.7 mmol) in tetrahydrofuran (25 ml) under an atmosphere of nitrogen at −78° C. was added a 1.5M solution of lithium diisopropylamidetetrahydrofuran complex in cyclohexane (5 ml). The reaction was stirred at −78° C. for 1 hour then 5-chloro-1,2,4-thiadiazole (950 mg, 7.9 mmol) was added. After 30 minutes the reaction was allowed to warm slowly to room temperature and the solvent was removed in vacuo. The residue was treated with methanol (15 ml) and 2N NaOH (15 ml) for 1.5 hours then the methanol was removed under reduced pressure and the remaining aqueous solution extracted three times with ethyl acetate. The aqueous solution was adjusted to pH1 using concentrated hydrochloric acid and allowed to stand for 3 hours then aqueous potassium carbonate was added and the solution extracted five times with dichloromethane. The combined extracts were dried with sodium sulphate and evaporated under reduced pressure to give a yellow oil (720 mg) was treated with oxalic acid (450 mg) in methanol, and evaporated to dryness. The residue was crystallised twice from methanol/propan-2-ol to give endo-3-[5-(1,2,4-thiadiazol)-yl]-1-azabicyclo[2.2.1]heptane hydrogen oxalate (200 mg), mp 140°-141° C.; (Found: C, 44.15; H, 4.83; N, 15.39. $C_8H_{11}N_3S \cdot (COOH)_2$ requires C, 44.27; H, 4.83; N, 15.49%); m/e 182 (CI+, [M+1]+ of free base); δ (360 MHz, $D_2O$) 1.62-1.71 (1H, m, one of $5CH_2$), 1.97-2.08 (1H, m, one of $5CH_2$), 3.34-3.60 (5H, m, 4CH, $6CH_2$ and $7CH_2$), 3.74 (1H, ddd, J=2.3, 6.0 and 12.2 Hz, one of $2CH_2$), 3.98 (1H, dt, J=3.0 and 12.1 Hz, one of $2CH_2$), 4.45-4.53 (1H, m, 3CH) and 8.75 (1H, s, thiadiazole H).

The mother liquor from the above crystallisation was treated with sodium methoxide (1 g) for two hours then the solvent was removed in vacuo. Water was added and extracted five times with dichloromethane. The combined extracts were dried and reduced to give a yellow oil which was treated with oxalic acid (350 mg) in methanol and concentrated to dryness. The residue was crystallised twice from methanol/diethyl ether to give exo-3-[5-(1,2,4-thiadiazol)-yl]-1-azabicyclo[2.2.1-]heptane hydrogen oxalate (435 mg), mp 121.5° C.; (Found: C, 44.14; H, 4.81; N, 15.39. $C_8H_{11}N_3S \cdot (COOH)_2$ requires C, 44.27; H, 4.83; N, 15.49%); m/e 182 (CI+, [M+1]+ of free base); δ (360 MHz $D_2O$) 1.98-2.08 (1H, m, one of $5CH_2$), 2.22-2.33 (1H, m, one of $5CH_2$), 3.25-3.32, 3.34-3.44 and 3.50-3.60 (2H, 1H and 2H respectively, each m, 4CH, $6CH_2$ and $7CH_2$), 3.82 (1H, ddd, J=2.0, 8.6 and 12.1 Hz, one of $2CH_2$), 3.89 (1H, ddd, J=2.8, 5.4 and 12.1 Hz, one of 2CH$_2$), 4.02–4.10 (1H, m, 3CH) and 8.72 (1H, s, thiadiazole H).

EXAMPLE 14 exo- and endo-3-[5-(3-Cyclopropyl-1,2,4-thiadiazol)-yl]-1-azabicyclo[2.2.1]heptane Hydrogen Oxalate These compounds were prepared by the method of Example 13 using 3-methoxycarbonyl-1-azabicyclo[2.2.1]heptane (1.5 g, 9.7 mmol) and 5-chloro-3-cyclopropyl-1,2,4-thiadiazole (2.0 g, 12.6 mmol) giving:

a) endo-3-[5-(3-Cyclopropyl-1,2,4-thiadiazol)-yl]-1-azabicyclo[2.2.1]heptane hydrogen oxalate (270 mg), mp 133°–134° C.; (Found: C, 49.64; H, 5.47; N, 13.38. C$_{11}$H$_{15}$N$_3$S.(COOH)$_2$.0.25H$_2$O requires C, 49.43; H, 5.58; N, 13.30%); m/e 221 (M$^+$ of free base); δ (360 MHz, D$_2$O) 1.07–1.16 (4H, m, 2×CH$_2$ of cyclopropyl); 1.62–1.72 and 1.98–2.10 (each 1H, each m, 5CH$_2$), 2.31–2.38 (1H, m, CH of cyclopropyl), 3.36–3.42 and 3.46–3.55 (3H and 2H respectively, each m, 4CH, 6CH$_2$ and 7CH$_2$), 3.67 (1H, ddd, J=2.3, 5.6 and 12.2 Hz, one of 2CH$_2$), 3.93 (1H, td, J=2.9 and 12.2 Hz, one of 2CH$_2$) and 4.37 (1H, m, 3CH).

b) exo-3-[5-(3-Cyclopropyl-1,2,4-thiadiazol)-yl]-1-azabicyclo[2.2.1]heptane hydrogen oxalate (105 mg), mp 159°–160° C.; (Found; C, 49.91; H, 5.49; N, 13.44. C$_{11}$H$_{15}$N$_3$S. (COOH)$_2$ requires C, 50.15; H, 5.50; N, 13.50%); m/e 221 (M$^+$ of free base); δ (360 MHz, D$_2$O) 1.04–1.14 (4H, m, 2×cyclopropyl CH$_2$), 1.95–2.10 and 2.20–2.36 (1H and 2H respectively, each m, 5CH$_2$ and cyclopropyl CH), 3.22 (1H, d, J=4.4 Hz, 4CH). 3.27 (1H, d, J=9.5 Hz, one of 7CH$_2$), 3.33–3.41 (1H, m, one of 6CH$_2$), 3.50–3.57 (1H, m, one of 6CH$_2$), 3.54 (1H, d, J=9.5 Hz, one of 7CH$_2$), 3.78–3.82 (2H, m, 2CH$_2$) and 3.91–3.95 (1H, m, 3CH).

EXAMPLE 15

3-[5-(3-Benzyl-1,2,4-thiadiazol)-yl]quinuclidine Hydrogen Oxalate

Reaction of 3-methoxycarbonylquinuclidine (1.69 g, 10 mmol) with 3-benzyl-5-chloro-1,2,4-thiadiazole (3.15 g, 15 mmol, prepared according to Chem. Ber., (1956), 89, 1534) by the method of Example 5 gave the title compound free base which was treated with oxalic acid and crystallised from methanol-diethyl ether to give the title compound (1.1 g), mp 88°–90° C.; (Found: C, 56.77, H, 5.75; N, 10.83. C$_{16}$H$_{19}$N$_3$S. (COOH)$_2$.0.45H$_2$O requires C, 56.36; H, 5.75; N, 10.96%); m/e 285 (M$^+$ of free base); δ (360 MHz, D$_2$O) 1.76–1.98 and 2.08–2.26 (each 2H, each m, 5CH$_2$ and 8CH$_2$), 2.46–2.52 (1H, m, 4CH), 3.29–3.50 (4H, m, 6CH$_2$ and 7CH$_2$), 3.74–3.88 (2H, m, 2CH$_2$), 4.03–4.10 (1H, m, 3CH), 4.34 (2H, s, CH$_2$Ph) and 7.23–7.43 (5H, m, Ph).

EXAMPLE 16

3-[5-(3-tert-Butyl-1,2,4-thiadiazol)-yl]quinuclidine Hydrogen Oxalate

The title compound free base was prepared from 3-methoxycarbonyl quinuclidine (1.5 g, 8.9 mmol) and 3-tert-butyl-5-chloro-1,2,4-thiadiazole (2.04 g, 11.5 mmol) by the method of Example 5. Treatment of the free base with oxalic acid and crystallisation from methanol-diethyl ether gave the title compound as a hygroscopic solid (120 mg); (Found: M$^+$=251.1445. C$_{13}$H$_{21}$N$_3$S (free base M$^+$) requires M$^+$ 251.1456); δ (360 MHz, D$_2$O) 1.41 (9H, s, 3×CH$_3$), 1.85–1.95 and 2.08–2.27 (each 2H, each m, 5CH$_2$ and 8CH$_2$), 2.50–2.56 (1H, m, 4CH), 3.28–3.54 (4H, m, 6CH$_2$ and 7CH$_2$), 3.80–3.90 (2H, m, 2CH$_2$) and 4.02–4.12 (1H, m, 3CH).

EXAMPLE 17 exo-3-[5-(3-Methyl-1,2,4-thiadiazol)-yl]-endo-5-hydroxy-1-azabicyclo[2.2.1]heptane a) trans-3,4-Dimethoxycarbonylpyrrolidine This was prepared from glycine and dimethylfumarate by the procedure reported by Joucla et al. J. Chem. Soc. Chem. Commun., (1985), 1566.

b) 1-Methoxycarbonylmethyl-trans-3,4-dimethoxycarbonyl pyrrolidine

A solution of trans-3,4-dimethoxycarbonylpyrrolidine (4.1 g, 22 mmol) in xylene (30 ml) was added to a rapidly stirred suspension of potassium carbonate (7 g) in xylene (150 ml), at 120° C. After 0.25 hour, a solution of methylbromoacetate (3.45 g, 22.5 mmol) in xylene (30 ml) was added dropwise and the mixture stirred rapidly at 140° C. for 2 hours. The solution was decanted from the inorganic residue which was taken up into water (100 ml) and extracted with dichloromethane (3×150 ml). The combined organics were dried (Na$_2$SO$_4$) and the solvent removed under vacuum to give the title triester as a yellow liquid (6 g); δ (360 MHz, CDCl$_3$) 2.96–3.11 (4H, m, 2CH$_2$ and 5CH$_2$), 3.31 (1H, d, J=16.5 Hz, one of NCH$_2$), 3.38 (1H, d, J=16.5 Hz, one of NCH$_2$), 3.46–3.52 (2H, m, 3CH and 4CH), 3.74 (9H, s, 3×CH$_3$).

c) 3-Methoxycarbonyl-5,5-dimethoxy-1-azabicyclo[2.2.1]heptane

A solution of 1-methoxycarbonylmethyl-trans-3,4-dimethoxycarbonylpyrrolidine (5 g, 19.31 mmol) in toluene (75 ml) was added dropwise over a 1 hour period to a rapidly stirred solution of potassium-t-butoxide (9 g, 80 mmol) in toluene (250 ml) at 130° C. The mixture was refluxed for 4 hours, cooled to room temperature and concentrated hydrochloric acid (75 ml) added dropwise and stirred for 0.25 hours. The organic phase was extracted with further portions of hydrochloric acid (3×50 ml) and the combined aqueous heated at 110° C. for 16 hours. The solvent was then removed in vacuo, the residue dried and taken up into methanol (saturated with hydrogen chloride, 150 ml). The mixture was stirred at room temperature for 24 hours and the solvent removed under vacuum. The residue was dissolved in water (50 ml), basified to pH>10 with potassium carbonate and extracted with dichloromethane (5×150 ml). The combined extracts were dried (Na$_2$SO$_4$) and the residue remaining after removal of the solvents was chromatographed through silica-gel, using dichloromethane/methanol (93:7) as eluant, to give the title ester as a yellow liquid (0.5 g). An analytical sample was prepared as the hydrogen oxalate salt, mp 134.5°–136.5° C. (propan-2-ol); (Found: C, 47.04; H, 6.20; N, 4.50. C$_{10}$H$_{17}$NO$_4$.(CO$_2$H)$_2$ requires C, 47.21; H, 6.27; N, 4.59%); δ (360 MHz, CDCl$_3$) 2.44 (1H, dd, J=9.8 and 3.2 Hz), 2.63 (1H, dd, J=12.7 and 3.2 Hz), 2.77 (1H, d, J=12.7 Hz), 2.80–3.10 (5H, m), 3.11 (3H, s, OCH$_3$), 3.24 (3H, s, OCH$_3$), 3.71 (3H, s, CO$_2$CH$_3$).

d) 3-[5-(3-Methyl-1,2,4-thiadiazol)-yl]-3-methoxycarbonyl-5,5-dimethoxy-1-azabicyclo[2.2.1]heptane Lithium diisopropylamide (4.7 ml of a 1.5M solution in tetrahydrofuran, 7.05 mmol) was added dropwise to a solution of 3-methoxycarbonyl-5,5-dimethoxy-1-azabicyclo[2.2.1]heptane (1 g, 4.7 mmol) in tetrahydrofuran (40 ml), at −78° C., and stirred for 2 hours. A solution of 5-chloro-3-methyl-1,2,4-thiadiazole (1 g, 7.4 mmol) in tetrahydrofuran (5 ml) was added to the reaction mixture at −78° C., stirred for 1 hour and then warmed to room temperature and stirred for 16 hours. Water (25 ml) and dichloromethane (70 ml) were added and the mixture extracted with dichloromethane (4×150 ml). The combined extracts were dried (Na$_2$SO$_4$), evaporated, and the crude product chromatographed through silica-gel using dichloromethane/methanol (95:5) as eluant to give the title compound (0.4 g) as a pale yellow oil, m/e 314 (CI$^+$, [M+1]$^+$); δ (360 MHz, CDCl$_3$) 2.64 (3H, s, CH$_3$), 2.74–2.85 and 2.97–3.02 (3H and 1H respectively, each m), 3.16 (3H, s, OCH$_3$), 3.27 (4H, s, 4CH and OCH$_3$), 3.70 (3H, s, CO$_2$CH$_3$), 3.68 (1H, dd J=12 7 and 1.5 Hz), 3.80 (1H, dd, J=12.7 and 3 Hz).

e) exo-3-[5-(3-Methyl-1,2,4-thiadiazol)-yl]-5,5-dimethoxy-1-azabicyclo[2.2.1]heptane Sodium hydroxide (6 ml of a 5N solution) was added to a solution of the preceding ester (0.4 g, 1.3 mmol) in methanol (2 ml) and heated at 70° C. for 1.5 hours. The solution was adjusted to pH1 with concentrated hydrochloric acid and stirred at room temperature for 16 hours. The methanol was removed under vacuum, dichloromethane (75 ml) added, and the aqueous basified with potassium carbonate. The residue remaining (0.2 g) after extraction into dichloromethane (4×75 ml), drying (Na$_2$SO$_4$) and removal of solvent under vacuum, was taken up into methanol (2 ml) and sodium methoxide (50 mg, 1 mmol) added. The solution was stirred at room temperature for 1 hour before removing the solvent under vacuum and chromatography of the residue through alumina using dichloromethane/methanol (97:3) as eluant to give exo-3-[5-(3-methyl-1,2,4-thiadiazol)-yl]-5,5-dimethoxy-1-azabicyclo[2.2.1]heptane (0.2 g); m/e 256 (CI$^+$, [M+1]$^+$); δ (360 MHz, CDCl$_3$) 2.45 (1H, dd, J=12.7 and 3.2 Hz), 2.64 (3H, s, CH$_3$), 2.78 (1H, dd, J=10.2 and 3.2 Hz), 2.90 (1H, s, 4CH), 2.95 (1H, d, J=12.7 Hz), 3.01 (1H, d, J=10.9 Hz), 3.10 (1H, dd, J=14 and 5 Hz), 3.19 (1H, m) 3.22 (3H, s, OCH$_3$), 3.27 (3H, s, OCH$_3$) and 3.70 (1H, m, 3CH).

f) exo-3-[5-(3-Methyl-1,2,4-thiadiazol)-yl]-1-alazabicyclo[2.2.1]heptan-5-one

A solution of exo-3-[5-(3-methyl-1,2,4-thiadiazol)-yl]-5,5-dimethoxy-1-azabicyclo[2.2.1]heptane (0.2 g, 0.8 mmol) in perchloric acid (3 ml of 70% solution in water) was heated at 65° C. for 2 hours. Water (20 ml) and dichloromethane (40 ml) were added to the reaction mixture and the aqueous basified with sodium carbonate. Extraction into dichloromethane (5×60 ml), drying (Na$_2$SO$_4$) and removal of solvent under vacuum gave the title ketone as a crystalline solid (0.14 g) mp 79°–83° C.; m/e 210 (CI$^+$, [M+1]$^+$); δ (360 MHz, CDCl$_3$) 2.66 (3H, s, CH$_3$), 2.93 (1H, dd, J=17.9 and 4.2 Hz), 3.07 (1H, s, 4CH), 3.12–3.16 (2H, m), 3.29–3.44 (3H, m) and 3.70–3.74 (1H, m, 3CH).

g) exo-3-[5-(3-Methyl-1,2,4-thiadiazol)-yl]-endo-5-hydroxy-1-azabicyclo[2.2.1]heptane Sodium borohydride (50 mg, 1.3 mmol) was added to a stirred solution of the preceding ketone (0.14 g, 0.7 mmol) in ethanol (10 ml), at 10° C. After 0.5 hours at 10° C. the solution was warmed to room temperature and stirred for a further 0.5 hours. Excess reagent was destroyed by addition of 2N hydrochloric acid and the solvents then removed under vacuum. The residue was taken up into water (15 ml), basified with potassium carbonate and extracted into dichloromethane (5×50 ml). The combined extracts were dried (Na$_2$SO$_4$) and the solvent removed under vacuum to give exo-3-[5-(3-methyl-1,2,4-thiadiazol)-yl]-endo-5-hydroxy-1-azabicyclo[2.2.1]heptane (0.1 g) as a crystalline solid, mp 127°–131° C. (ethyl acetate); (Found: C, 51.14; H, 6.22; N, 19.88. C$_9$H$_{13}$N$_3$SO requires C, 51.15; H, 6.20; N, 19.89%); m/e 212 (CI$^+$, [M+1]$^+$). δ (360 MHz, CDCl$_3$) 1.8–2.1 (1H, broad s, OH), 2.18 (1H, dt, J=3.6 and 12.6 Hz, endo 6CH), 2.64 (3H, s, CH$_3$), 2.66 (1H, d, J=11.5 Hz, one of 7CH$_2$), 2.84 (1H, dd, J=3.6 and 11.5 Hz, one of 7CH$_2$), 2.86 (1H, d, J=4.8 Hz, 4CH), 3.11–3.20 (2H, m, exo 2CH and exo 6CH), 3.27 (1H, ddd, J=2.5, 8.0 and 12.0 Hz, endo 2CH), 4.08 (1H, dd, J=6.2 and 8.0 Hz, 3CH) and 4.53 (1H, quintet, J=3.6 Hz, 5CH).

EXAMPLE 18

3-[5-(3-iso-Propyl-1,2,4-thiadiazol)-yl]quinuclidine Hydrogen Oxalate

The title compound free base was prepared from 3-methoxycarbonyl quinuclidine (2.0 g, 11.8 mmol) and 5-chloro-3-iso-propyl-1,2,4-thiadiazole (2.5 g, 15.4 mmol) by the method of Example 5. Treatment with oxalic acid and crystallisation from dichloromethanediethyl ether gave the title compound (380 mg), mp 115°–117° C.; (Found: C, 51.29; H, 6.37; N, 12.69. C$_{12}$H$_{19}$N$_3$S.(COOH)$_2$ requires C, 51.36; H, 6.46; N, 12.83%); m/e 237 (M$^+$ of free base); δ (360 MHz, D$_2$O) 1.33 and 1.35 (each 3H, each s, 2×CH$_3$), 1.88–1.93 and 2.10–2.22 (each 2H, each m, 5CH$_2$ and 8CH$_2$), 2.51–2.56 (1H, m, 4CH), 3.30–3.50 (5H, m, 6CH$_2$, 7CH$_2$ and CH(CH$_3$)$_2$), 3.81 (1H, ddd, J=1.9, 7 and 13 Hz, one of 2CH$_2$), 3.87 (1H, ddd, J=2.4, 10 and 13 Hz, one of 2CH$_2$) and 4.08 (1H, ddd, J=2.4, 7 and 10 Hz, 3CH).

EXAMPLE 19 exo- and endo-3-[5-(3-Ethyl-1,2,4-thiadiazol)-yl]-1-azabicyclo[2.2.1]heptane Hydrogen Oxalate Reaction of 3-methoxycarbonyl-1-azabicyclo[2.2.1]heptane (1.37 g, 8.8 mmol) with 5-chloro-3-ethyl-1,2,4-thiadiazole (1.7 g, 11.5 mmol) by the method of Example 13 gave:

a) endo-3-[5-(3-Ethyl-1,2,4-thiadiazol)-yl]-1-azabicyclo[2.2.1]heptane hydrogen oxalate (370 mg), mp 142°–143° C.; (Found: C, 48.14; H, 5.69; N, 14.03. C$_{10}$H$_{15}$N$_3$S.(COOH)$_2$ requires C, 48.15; H, 5.72; N, 14.04%); m/e 209 (M$^+$ of free base); δ (360 MHz, D$_2$O) 1.32 (3H, t, J=7.6 Hz, CH$_3$); 1.62–1.72 and 1.98–2.10 (each 1H, each m, 5CH$_2$), 3.00 (2H, q, J=7.6 Hz, CH$_2$CH$_3$), 3.32–3.60 (5H, m, 4CH, 6CH$_2$ and 7CH$_2$), 3.67 (1H, ddd, J=2.2, 5.7 and 12.0 Hz, one of 2CH$_2$), 3.98 (1H, dt, J=2.9 and 12.0 Hz, one of 2CH$_2$) and 4.34–4.42 (1H, m, 3CH).

b) exo-3-[5-(3-Ethyl-1,2,4-thiadiazol)-yl]-1-azabicyclo[2.2.1]heptane hydrogen oxalate (370 mg), mp 133°–135° C.; (Found: C, 48.00; H, 5.64; N, 13.98. C$_{10}$H$_{15}$N$_3$S.(COOH)$_2$ requires C, 48.15; H, 5.72; N, 14.04%); m/e 209 (M$^+$ of free base); δ (360 MHz, D$_2$O) 1.31 (3H, t, J=7.6 Hz, CH$_3$), 1.98–2.10 and 2.22–2.34 (each 1H, each m, 5CH$_2$), 2.97 (2H, q, J=7.6 Hz, CH$_2$CH$_3$), 3.26 (1H, d, J=5 Hz, 4CH), 3.29 (1H, d, J=10 Hz, one of 7CH$_2$), 3.32–3.43 (1H, m, one of 6CH$_2$), 3.52 (1H, d, J=10 Hz, one of 7CH$_2$), 3.50–3.58 (1H, m, one of 6CH$_2$), 3.82 (2H, d, J=7.2 Hz, 2CH$_2$) and 3.98 (1H, t, J=7.2 Hz, 3CH).

EXAMPLE 20

1-Methyl-3-[5-(1,2,4-thiadiazol)-yl]-1,2,5,6-tetrahydropyridine Hydrochloride a) 3-[5-(1,2,4-Thiadiazol)-yl]pyridine Thionicotinamide (7.8 g, 56.5 mmol) suspended in dichloromethane (200 ml) was stirred with dimethylformamide dimethyl acetal (20 ml) for two days. The solvent was removed under reduced pressure and the residue treated with hydroxylamine-O-sulphonic acid (9.6 g, 85 ml) in methanol (125 ml) for 15 hours, in the presence of pyridine (9 ml, 113 mmol). The reaction mixture was concentrated under reduced pressure, aqueous $K_2CO_3$ was added and the mixture then extracted with dichloromethane three times. The combined extracts were dried with sodium sulphate and evaporated to give a residue which was purified by chromatography on alumina eluting with diethyl ether. Crystallisation from diethyl ether-hexane gave the title compound (730 mg), mp 83°–84° C.; (Found: C, 51.56; H, 3.21; N, 25.65. $C_7H_5N_3S$ requires C, 51.52; H, 3.09; N, 25.75%); m/e 163 (M+); δ (360 MHz, $CDCl_3$) 7.48 (1H, ddd, J=0.7, 4.9 and 7.9 Hz, 5CH), 8.29 (1H, dt, J=2.0 and 7.9 Hz, 4CH), 8.68–8.72 (2H, m, 6CH and thiadiazole H) and 9.21 (1H, d, J=2.0 Hz).

b) 1-Methyl-3-[5-(1,2,4-thiadiazol)-yl]-1,2,5,6-tetrahydropyridine Hydrochloride The foregoing pyridine derivative (310 mg, 1.96 mmol) in acetone (4 ml) was stirred with iodomethane (0.25 ml) for 3 days. The reaction mixture was diluted with diethyl ether (20 ml) and filtered to give a yellow solid which was dissolved in ethanol (5 ml) and water (5 ml). Sodium borohydride (85 mg) was added in portions over 15 minutes while cooling the mixture at 0° C. After further stirring for 1 hour the reaction was extracted four times with diethyl ether and the combined extracts dried and concentrated in vacuo. The residue was treated with ethereal hydrogen chloride, evaporated to dryness, then dissolved in methanol and stirred with activated charcoal for 1 hour. The mixture was filtered and concentrated to give a solid which was recrystallised from methanol-diethyl ether yielding the title compound (125 mg). mp 134° C. (decomp.); (Found: C, 44.05; H, 5.49; N, 19.26. $C_8H_{11}N_3S\cdot HCl$ requires C, 44.13; H, 5.55; N, 19.30%); m/e 181 (M+ of free base); δ (360 MHz, $D_2O$) 2.77–2.84 (2H, m, $5CH_2$), 3.09 (3H, s, $CH_3$), 3.42–3.62 (2H, broad s, $6CH_2$), 4.19–4.38 (2H, broad s, $2CH_2$), 7.11–7.15 (1H, m, 4CH) and 8.73 (1H, s, thiadiazole H).

EXAMPLE 21

3-[5-(1,2,4-Thiadiazol)-yl]-1,2,5,6-tetrahydropyridine Hydrochloride

1-Methyl-3-[5-(1,2,4-thiadiazol)-yl]-1,2,5,6-tetrahydropyridine (95 mg, 0.52 mmol) was heated under reflux for 2 hours with vinyl chloroformate (65 μl, 0.75 mmol) in 1,2 dichloroethane (2 ml). After cooling, water (5 ml) and 2N hydrochloric acid (0.5 ml) was added and the mixture extracted 3 times with diethyl ether. The combined extracts, dried and evaporated in vacuo, gave an oil which was treated with methanolic hydrogen chloride for 2 hours. The solvent was evaporated off and the residue treated with activated charcoal in methanol for 15 minutes, filtered and concentrated. Crystallisation from methanol-diethyl ether gave the title compound (23 mg), mp 237° C. (decomp.); (Found: C, 40.77; H, 5.12; N, 20.03. $C_7H_9N_3S\cdot HCl\cdot 0.25H_2O$ requires C, 40.38; H, 5.08; N, 20.18%); m/e 167 (M+ of free base); δ (360 MHz, $D_2O$) 2.69–2.75 (2H, m, $5CH_2$), 3.47 (2H, t, J=6.2 Hz, $6CH_2$), 4.23 (2H, d, J=2 Hz, $2CH_2$), 7.12–7.16 (1H, m, 4CH) and 8.72 (1H, s, thiadiazole H).

EXAMPLE 22

1-Methyl-3-[5-(3-methyl-1,2,4-thiadiazol)-yl]-1,2,5,6-tetrahydropyridine Hydrochloride a) 3-[5-(3-methyl-1,2,4-thiadiazol)-yl]pyridine.

This compound was prepared from thionicotinamide and dimethylacetamide dimethylacetal by the method of Example 20 and obtained as an oil after chromatography on silica gel; δ (360 MHz, $CDCl_3$) 2.76 (3H, s,$CH_3$), 7.45 (1H, ddd, J=1.2, 7.0 and 11.4 Hz, 5CH), 8.24 (1H, ddd, J=2.3, 3.2 and 11.4 Hz, 4CH), 8.75 (1H, dd, J=2.3 and 7.0 Hz, 6CH) and 9.17 (1H, dd, J=1.2 and 3.2 Hz, 2CH).

b) 1-Methyl-3-[5-(3-methyl-1,2,4-thiadiazol)-yl]-1,2,5,6-tetrahydropyridine Hydrochloride The title compound was prepared from the foregoing pyridyl-thiadiazole by the method of Example 20 and obtained as a white crystalline solid, mp 182° (decomp.); (Found: C, 45.43; H, 6.04; N, 17.63. $C_9H_{13}N_3S\cdot HCl\cdot 0.33H_2O$ requires C, 45.78; H, 6.22; N, 17.68%); m/e 195 (M+ of free base); δ (250 MHz, $D_2O$) 2.62 (3H, s, thiadiazole $CH_3$), 2.74–2.85 (2H, m, $5CH_2$), 3.09 (3H, s, $NCH_3$), 3.30–3.46 (1H, m, one of $6CH_2$), 3.64–3.76 (1H, m, one of $6CH_2$), 4.09 (1H, dd, J=2.4 and 16.0 Hz, one of $2CH_2$), 4.42 (1H, d, J=16.0 Hz, one of $2CH_2$) and 7.03–7.10 (1H, m, 4CH).

EXAMPLE 23

3-[5-(3-Methyl-1,2,4-thiadiazol)-yl]-1,2,5,6-tetrahydropyridine Hydrochloride 1-Methyl-3-[5-(3-methyl-1,2,4-thiadiazol)-yl]-1,2,5,6-tetrahydropyridine was treated with vinyl chloroformate and then methanolic hydrogen chloride by the method of Example 21 to give the title compound, mp 177° C. (decomp.); (Found; C. 41.05; H, 5.33; N, 17.86. $C_8H_{11}N_3S\cdot 1.5HCl$ requires C, 40.72; H, 5.34; N, 17.81%); m/e 181 (M+ of free base); δ (360 MHz, $D_2O$) 2.63 (3H, s, $CH_3$), 2.68–2.76 (2H, m, $5CH_2$), 3.47 (2H, t, J=6.2 Hz, $6CH_2$), 4.17–4.22 (2H, m, $2CH_2$) and 7.03–7.10 (1H, m, 4CH).

EXAMPLE 24

3-[5-(3-(1-Hydroxy-1-phenylmethyl)-1,2,4-thiadiazol)-yl]quinuclidine Hydrogen Oxalate a) α-(Tetrahydropyranyloxy)-phenylacetamidine Hydrochloride To a solution of sodium (230 mgs, 10 mmol) in dry ethanol was added α-(tetrahydropyranyloxy)benzylcyanide (21.7 g, 100 mmol, J. R. Anderson, R. L. Edwards and A. J. S. Whalley, JCS Perkin I, 215, (1982)). After stirring for 16 hours the reaction was cooled to −50° C. and 50 ml of dry ammonia (50 ml) was condensed into the solution. Dry ammonium chloride (5.3 g, 100 mmol) was added and the reaction allowed to warm to room temperature overnight. After filtration and evaporation of the solvents the residue was taken up into water (200 ml), washed with dichloromethane (2×200 ml) and evaporated to give a white solid (22.9 g) mp 53°–55° C.; m/e 235 (M+H)+; δ (360 MHz; $D_2O$) 1.50–1.86 (6H, m, 3×$CH_2$); 3.49–3.53, 3.60–3.69 and 3.91–3.96 (0.5H, 1H and 0.5H respectively, $CH_2O$); 4.64 and 5.00 (each 0.5H, each t, J=7 Hz, CHO—); 5.61 and 5.64 (each 0.5H, each s, PhCH); 7.47–7.61 (5H, m, C₆H₅).

b) 3-(1-Phenyl-1-tetrahydropyranyloxymethyl)-5-chloro-1,2,4-thiadiazole

The foregoing amidine (22.8 g, 85 mmol) was dissolved in cold 4.2N sodium hydroxide solution (120 ml, 0.5 mol) and a solution of perchloromethyl mercaptan (19.5 g, 110 mmol) in dichloromethane (120 ml) was added to the vigorously stirred reaction mixture over 1 hour. After a further hour the organic layer was separated and the aqueous solution was reextracted three times with dichloromethane to give an oil which was purified by silica gel chromatography eluting with hexane-diethyl ether to give the title compound (10.0 g); m/e 209 (M–C$_5$H$_9$O$_2$)$^+$; (Found: C, 54.49; H, 4.96; N, 8.92; C$_{14}$H$_{15}$N$_2$O$_2$SCl requires C, 54.10; H, 4.86; N, 9.01%); δ (360 MHz, CDCl$_3$) 1.51–1.93 (6H, m, 3×CH$_2$); 3.46–3.54; 3.73–3.80 and 3.88–3.94 (1H, 0.5H and 0.5H, respectively, each m, CH$_2$O); 4.69 and 4.84 (each 0.5H, t, J=3 Hz, CHO—); 6.04 and 6.09 (each 0.5H, each s, PhCH); 7.25–7.55 (5H, m, Ph).

c) 3-[5-(3-(1-Hydroxy-1-phenylmethyl)-1,2,4-thiadiazol)-yl]quinuclidine Hydrogen oxalate.

Reaction of 3-methoxycarbonyl quinuclidine (4.0 g, 24 mmol) with 3-(1-phenyl-1-tetrahyropyranyloxymethyl)-5-chloro-1,2,4-thiadiazole (7.75 g, 24 mmol) by the method of Example 5 gave the title compound free base (1.1 g, 15%) which was treated with oxalic acid to give the hydrogen oxalate salt (1.4 g); mp=61°–62° C.; m/e 301 (M+ of free base); δ (360 MHz, D$_2$O) 1.70–1.90 and 2.06–2.25 (each 2H, each m, 5CH$_2$ and 8CH$_2$), 1.45–1.52 (1H, m, 4CH), 3.24–3.47 (4H, m, 6CH$_2$ and 7CH$_2$), 3.73–3.87 (2H, m, 2CH$_2$), 4.06–4.13 (1H, m, 3CH), 6.14 (1H, s, CHOH) and 7.36–7.50 (5H, m, Ph).

EXAMPLE 25

3-[5-(3-Benzoyl-1,2,4-thiadiazol)-yl]-quinuclidine Hydrogen oxalate

3-[5-(3-(1-Hydroxy-1-phenylmethyl)-1,2,4-thiadiazol)-yl]quinuclidine (1.0 g, 3.3 mmol) in dichloromethane (50 ml) was stirred with activated manganese dioxide (5 g). After 0.5 hour, the reaction was filtered and the manganese dioxide repeatedly washed with dichloromethane. The combined extracts were evaporated to yield the title compound free base (1.0 g) which was treated with oxalic acid. Crystallisation from diethyl ether gave the title compound, mp 95°–97° C. (decomp.); m/e 299 (M+ of free base); (Found: C, 53.94; H, 5.15; N, 10.20; C$_{16}$H$_{17}$N$_3$OS.(COOH)$_2$.0.6H$_2$O requires C, 54.02; H, 5.09; N, 10.49%); δ (360 MHz, D$_2$O) 1.92–1.98 and 2.16–2.34 (each 2H, each m, 5CH$_2$ and 8CH$_2$), 2.58–2.62 (1H, m, 4CH), 3.36–3.58 (4H, m, 6CH$_2$ and 7CH$_2$), 3.84–4.04 (2H, m, 2CH$_2$), 4.22–4.30 (1H, m, 3CH), 7.62 (2H, t, J=8 Hz, 3H and 5H of Ph), 7.79 (1H, t, J=8 Hz, 4H of Ph) and 8.13 (2H, d, J=8 Hz, 2H and 6H of Ph).

EXAMPLE 26

3-[5-(3-(1,1-Diphenyl-1-hydroxymethyl)-1,2,4-thiadiazol)-yl]quinuclidine Hemi-Hydrogen Oxalate 3-[5-(3-Benzoyl-1,2,4-thiadiazol)-yl]-quinuclidine (0.92 g, 3.1 mmol) in dry tetrahydrofuran (50 ml) under an atmosphere of dry nitrogen was treated with phenyl magnesium bromide (3 ml of a 3M solution in diethyl ether) at room temperature for 2 hours. Saturated ammonium chloride solution was added and the mixture partitioned and extracted twice with dichloromethane. The combined organic solutions were dried and concentrated to give a residue which was purified by chromatography to yield the title compound free base an oil (633 mg). Treatment with oxalic acid in diethyl ether gave the title compound, mp 185°–186° C.; (Found: C, 63.22; H, 5.71; N, 9.55. C$_{22}$H$_{23}$N$_3$OS. (COOH). 0.9H$_2$O requires C, 62.96; H, 5.93; N, 9.58%); m/e 377 (M+ of free base); δ (360 MHz, D$_2$O) 1.72–1.96 and 2.04–2.26 (each 2H, each m, 5CH$_2$ and 8CH$_2$), 2.46–2.50 (1H, m, 4CH), 3.26–3.40 (4H, m, 6CH$_2$ and 7CH$_2$), 3.73–3.83 (2H, m, 2CH$_2$), 4.10–4.15 (1H, m, 3CH) and 7.31–7.42 (10H, m, 2×Ph).

EXAMPLE 27

3-[5-(3-(1,1-Diphenyl-1-fluoromethyl)-1,2,4-thiadiazol)-yl]quinuclidine Hydrogen Oxalate 3-[5-(3-(1,1-Diphenyl-1-hydroxymethyl)-1,2,4-thiadiazol)-yl]quinuclidine (377 mg, 1 mmol) in dichloromethane (5 ml) was treated with diethylamino sulphurtrifluoride (1.7 g, 6.3 mmol) at −78° C. The reaction was allowed to warm slowly to room temperature then aqueous potassium carbonate was added and extracted with dichloromethane. The extracts were dried and concentrated in vacuo to give an oil which was treated with oxalic in diethylether yielding the title compound, mp 114°–115° C.; (Found: C, 59.34; H, 5.26; N, 8.65. C$_{22}$H$_{22}$N$_3$FS.(COOH)$_2$. H$_2$O requires C, 59.13; H, 5.38; N, 8.62%); m/e 379 (M+ of free base); δ (360 MHz, D$_2$O) 1.64–1.90 and 2.02–2.25 (each 2H, each m, 5CH$_2$ and 8CH$_2$), 2.42–2.52 (1H, m, 4CH), 3.18–3.44 (4H, m, 6CH$_2$ and 7CH$_2$), 3.67–3.90 (2H, m, 2CH$_2$), 4.07–4.18 (1H, m, 3CH) and 7.24–7.50 (10H, m, 2×Ph).

EXAMPLE 28

6-[5-(3-Methyl-1,2,4-thiadiazol)-yl]-1-azabicyclo-[3.2.1.]octane a) 1-Ethoxycarbonylmethyl-3-ethoxycarbonylpiperidine Ethyl bromoacetate (21.2 g, 0.127 mol) was added dropwise to a solution of 3-methoxycarbonylpiperidine (40 g, 0.254 mol) in diethyl ether (250 ml) at 0° C. The reaction was heated under reflux for 1 hour and the resulting precipitate filtered off and washed with diethyl ether. The ethereal solution was concentrated under reduced pressure to give the title compound (27.6 g); δ (60 MHz, CDCl$_3$) 1.25 and 1.27 (each 3H, each t, J=7 Hz, 2×OCH$_2$CH$_3$). 1.40–3.70 (9H, m, 2CH$_2$, 3CH, 4CH$_2$, 5CH$_2$ and 6CH$_2$), 3.20 (2H, s, NCH$_2$CO$_2$), 4.10 and 4.15 (each 2H, each q, J=7 Hz, 2×NCH$_2$CO$_2$).

b) 1-Azabicyclo[3.2.1]octan-6-one

The foregoing diester (30.0 g, 0.123 mol) in toluene (300 ml) was added dropwise to a solution of potassium tert-butoxide (41.4 g, 0.37 mmol) in toluene (1l) at reflux under an atmosphere of nitrogen with vigorous stirring. After complete addition (2.5 hours) the reaction was allowed to cool and the solvent decanted from the resulting solid. The solid was heated under reflux in concentrated hydrochloric acid (600 ml) for 16 hours then reduced under high vacuum. The residue was added to aqueous potassium carbonate which was extracted (3×) with dichloromethane. The combined extracts were dried (Na$_2$SO$_4$) and concentrated to give the title compound (8.8 g) as a crystalline solid, mp 83°–87° C.; m/e 125 (M+); δ (360 MHz, CDCl$_3$) 1.3–2.4 (5H, m, 3CH$_2$, 4CH$_2$ and 5CH), 2.6–3.6 (6H, m, 2CH$_2$, 7CH$_2$ and 8CH$_2$).

c) 6-(1,3-Dithian-2-ylidene)-1-azabicyclo[3.2.1]-octane n-Butyl lithium (6.05 ml of a 1.6M solution in hexane, 9.7 mmol) was added dropwise to a solution of 2-trimethylsilyl-1,3-dithiane (1.86 g, 9.7 mmol) in tetrahydrofuran (30 ml) at −30° C. and the reaction mixture stirred for 2 hours. A solution of 1-azabicyclo[3.2.1]octan-6-one (1.1 g, 8.8 mmol) in tetrahydrofuran (10 ml) was added dropwise and the reaction mixture allowed to warm to room temperature. Water (20 ml) was added and extracted (3×) with dichloromethane. The combined extracts were dried (MgSO$_4$) and concentrated and the residue purified by chromatography on alumina eluting with dichloromethane/methanol (97:3) to give the title compound as a colourless oil (2 g); m/e 227 (M$^+$); δ (360 MHz, CDCl$_3$) 1.23–1.38 and 1.56–1.86 (1H and 3H respectively, each m, 3CH$_2$ and 4CH$_2$), 2.08–2.24 (2H, m, SCH$_2$CH$_2$), 2.76–3.00 (9H, m, 2×SCH$_2$, 2CH$_2$, 5CH and 8CH$_2$), 3.42 (1H, d, J=17 Hz, one of 7CH$_2$) and 3.56 (1H, d, J=17 Hz, one of 7CH$_2$).

d) 6-Methoxycarbonyl-1-azabicyclo[3.2.1]octane

The preceding compound (2.0 g, 8.8 mmol) was stirred in methanolic hydrogen chloride (75 ml) at 55° C. for 5 hours then the solvent was removed in vacuo. The residue was treated with potassium carbonate solution and extracted (4×) with dichloromethane. The combined extracts were dried (Na$_2$SO$_4$) and concentrated to give the title compound as an oil (0.5 g), characterised as the hydrochloride salt, mp 151°–154° C.; (Found: C, 51.92; H, 7.65; N, 6.83. C$_9$H$_{16}$NO$_2$Cl. 0.125H$_2$O requires: C, 51.98, H, 7.82; N, 6.73%); δ (360 MHz, D$_2$O) 1.30–1.41 and 1.54–1.72 (1H and 3H respectively, each m, 3CH$_2$ and 4CH$_2$), 2.41–2.48 (1H, m, 5CH), 2.78–2.87 (5H, m, 2CH$_2$, 6CH and 8CH$_2$), 3.05–3.20 (2H, m, 7CH$_2$) and 3.68 (3H, s, CH$_3$).

e) 6-[5-(3-Methyl-1,2,4-thiadiazol)-yl]-1-azabicyclo[3.2.1]octane

The foregoing ester (6.0 g, 35.5 mmol) in tetrahydrofuran (250 ml) was treated with lithium diisopropylamide-tetrahydrofuran complex (35.5 ml of a 1.5M solution in cyclohexane, 53.3 mmol) at −78° C. under an atmosphere of nitrogen. After 1 hour 5-chloro-3-methyl-1,2,4-thiadiazole (7.17 g, 53.3 mmol) was added and the reaction allowed to warm slowly to room temperature over 3 hours. The solvent was removed under reduced pressure and the residue in aqueous potassium carbonate extracted with dichloromethane. The combined extracts were dried and concentrated and the residue stirred in methanol (80 ml) and 2N NaOH (80 ml) for 2 hours. The methanol was evaporated off and the aqueous solution extracted with ethyl acetate (3×). The remaining aqueous solution was adjusted to pH2 for 2 hours then made basic with potassium carbonate and extracted (3×) with dichloromethane. The combined extracts, dried and concentrated, gave an oil which was treated with sodium methoxide (250 mg) in methanol (5 ml) for 1 hour. The solvent was removed in vacuo and the residue purified by chromatography on alumina (eluting with methanol/dichloromethane (2:98) to give the title compound (80 mg), mp 62°–63° C.; (Found: C, 57.5; H, 7.3; N, 19.8. C$_{10}$H$_{15}$N$_3$S requires: C, 57.4; H, 7.2; N, 20.1%); m/e 209 (M$^+$); δ (360 MHz, CDCl$_3$) 1.64–1.84 (4H, m, 3CH$_2$ and 4CH$_2$), 2.46–2.50 (1H, m, 5CH), 2.64 (3H, s, CH$_3$), 2.87–3.04 (4H, m, 2CH$_2$ and 8CH$_2$), 3.15 (1H, dd, J=5 and 13 Hz, one of 7CH$_2$), 3.52 (1H, ddd, J=2, 8 and 13 Hz, one of 7CH$_2$), 3.68 (1H, dd, J=5 Hz and 8 Hz, 6CH).

EXAMPLE 29

3-[5-(3-Dimethylamino-1,2,4-thiadiazol)-yl]-1-methyl-1,2,5,6-tetrahydropyridine Dihydrochloride a) 3-[5-(3-Dimethylamino-1,2,4-thiadiazol)-yl]pyridine Methyl thiononicotinate (6.0 g, 22.6 mmol, prepared according to H. Budzikiewicz et al., *Phosphorus and Sulphurs*, (1981), 11, 33) in methanol (100 ml) was heated under reflux for 16 hours with 1,1-dimethylguanidine sulphate (26.7 g, 21.5 mmol) and sodium methoxide (5.3 g, 43.0 mmol). The reaction was then cooled, filtered and concentrated in vacuo. The residue was dissolved in methanol (100 ml) and treated with bromine (2.9 ml, 56.6 mmol added dropwise in 20 ml dichloromethane). The reaction was concentrated under reduced pressure, aqueous K$_2$CO$_3$ was added to the residue and extracted four times with dichloromethane. The combined extracts were dried (Na$_2$SO$_4$), concentrated and the residue purified by chromatography through silica eluting with ethyl acetate/hexane to give the title compound (3.4 g), mp 48°–49° C.; (Found: C, 52.33; H, 4.89; N, 27.16. C$_9$H$_{10}$N$_4$S requires C, 52.41; H. 4.92; N, 27.47%); m/e 206 (M$^+$); δ (360 MHz, CDCl$_3$) 3.27 (6H, s, 2×CH$_3$), 7.42 (1H, dd, J=5 and 7 Hz, 5CH), 8.18 (1H, dt, J=2 and 7 Hz, 4CH), 8.72 (1H, d, J=5 Hz, 6CH) and 9.12 (1H, d, J=2 Hz, 2CH).

b) 3-[5-(3-Dimethylamino-1,2,4-thiadiazol)-yl]-1-methyl-1,2,5,6-tetrahydropyridine Dihydrochloride The foregoing pyridyl-thiadiazole (3.1 g, 15 mmol) was quaternised with methyl iodide then reduced with sodium borohydride by the method of Example 20 to give the title compound (100 mg), mp 164°–165° C. (methanol-diethyl ether); (Found: C, 40.12; H, 5.84; N, 18.47. C$_{10}$H$_{16}$N$_4$S. 2HCl requires C, 40.41; H, 6.10; N, 18.85%); m/e 224 (M$^+$ of free base); δ (360 MHz, D$_2$O) 2.72–2.82 (2H, m, 5CH$_2$), 3.06 (3H, s, NCH$_3$), 3.14 (6H, s, 2×NCH$_3$), 3.30–3.38 and 3.64–3.72 (each 1H, each m, 6CH$_2$), 4.06 (1H, dm, J=16 Hz, one of 2CH$_2$), 4.44 (1H, d, J=16 Hz, one of 2CH$_2$) and 7.94–7.98 (1H, m, 4CH).

EXAMPLE 30

3-[5-(3-Dimethylamino-1,2,4-thiadiazol)-yl]1,2,5,6-tetrahydropyridine Hydrochloride Treatment of 3-[5-(3-Dimethylamino-1,2,4-thiadiazol)-yl]-1-methyl-1,2,5,6-tetrahydropyridine with vinyl chloroformate then methanolic hydrogen chloride by the method of Example 21 gave the title compound, mp 203°–204° C.; (Found: C, 42.34; H, 5.92; N, 21.40. C$_9$H$_{14}$N$_4$S. 1.3HCl requires: C, 41.95; H, 5.98; N, 21.74%); (Found: M$^+$=210.0930. C$_9$H$_{14}$N$_4$S requires: M$^+$=210.0939); δ (360 MHz, D$_2$O) 2.64–2.72 (2H, m, 5CH$_2$), 3.15 (6H, s, 2×CH$_3$), 3.46 (2H, t, J=6.2 Hz, 6CH$_2$), 4.16–4.20 (2H, m, 2CH$_2$) and 6.94–7.00 (1H, m, 4CH).

EXAMPLE 31

1-Methyl-3-[5-(3-methylamino-1,2,4-thiadiazol)-yl]-1,2,5,6-tetrahydropyridine Hydrogen Oxalate The title compound free base was prepared from methyl thiononicotinate and methyl guanidine by the method of Example 29. Treatment with oxalic acid and crystallisation from methanol-diethyl ether gave the title compound, mp 155°–156° C. (decomp.); (Found: C, 43.60; H, 5.44; N, 17.83. C$_9$H$_{14}$N$_4$S. 1.1 (COOH)$_2$ requires: C, 43.49; H, 5.28; N, 18.11%); m/e 210 (M$^+$ of free base); δ (360 MHz, D$_2$O) 2.70–2.80 (2H, m, 5CH$_2$), 2.92 (3H, s, NCH₃), 3.05 (3H, s, NHCH₃), 3.27–3.36 (1H, m, one of 6CH$_2$), 3.62–3.69 (1H, m, one of 6CH$_2$), 4.03 (1H, broad d, J=16 Hz, one of 2CH$_2$), 4.37 (1H, broad d, J=16 Hz, one of 2CH$_2$) and 6.92–6.97 (1H, m, 4CH).

EXAMPLE 32

3-[5-(3-Ethylamino-1,2,4-thiadiazol)-yl-1-methyl-1,2,5,6-tetrahydropyridine Hydrochloride The title compound was prepared from methyl thiononicotinate and ethyl guanidine by the method of Example 29 and obtained as a white crystalline solid, mp 216°–217° C. (decomp.); (Found: C, 45.43; H, 6.44; N, 21.14. $C_{10}H_{16}N_4S.HCl.0.25H_2O$ requires: C, 45.27; H, 6.65; N, 21.12%); m/e 224 (M+ of free base); δ (360 MHz, D$_2$O) 1.22 (3H, t, J=7.2 Hz, CH$_2$CH$_3$), 2.74–2.82 (2H, m, 5CH$_2$), 3.08 (3H, s, NCH$_3$), 3.37 (2H, t, J=7.2 Hz, NCH$_2$CH$_3$), 3.4–3.6 (2H, broad signal, 6CH$_2$), 4.1–4.3 (2H, broad signal, 2CH$_2$), 6.95–7.00 (1H, m, 4CH).

EXAMPLE 33 exo-3-[5-(3-Dimethylamino-1,2,4-thiadiazol)-yl]-endo-5-hydroxy-1-azabicyclo[2.2.1]heptane Hemi-Hydrogen Oxalate a) 3-[5-(3-Dimethylamino-1,2,4-thiadiazol)-yl]-3-methoxycarbonyl-5,5-dimethoxy-1-azabicyclo[2.2.1]heptane The title compound was obtained as an orange oil (250 mg) from 3-methoxycarbonyl-5,5-dimethoxy-1-azabicyclo[2.2.1]heptane (2.0 g, 9.3 mmol) and 5-chloro-3-dimethylamino-1,2,4-thiadiazole (1.98 g, 12 mmol) the method of Example 17d; m/e 342 (M+), (Found: M+=342.1386; $C_{14}H_{22}N_4O_4S$ requires M+=342.1362); δ (360 MHz, CDCl$_3$) 2.77 (1H, dd, J=3 and 13 Hz), 2.82 (1H, d, J=13 Hz), 2.89 (1H, dd, J=3 and 10 Hz), 3.04 (1H, d, J=10 Hz), 3.15 (9H, s, OCH$_3$ and N(CH$_3$)$_2$), 3.20 (1H, s, 4CH), 3.26 (3H, s, OCH$_3$), 3.72 (3H, s, CO$_2$CH$_3$), 3.73 (2H, s).

b) exo-3-[5-(3-Dimethylamino-1,2,4-thiadiazol)-yl]-5,5-dimethoxy-1-azabicyclo[2.2.1]heptane A solution of sodium hydroxide (280 mg, 7 mmol) in water (2 ml) was added to a solution of the preceding ester (240 mg, 0.7 mmol) in methanol (2 ml) and the reaction mixture was stirred at 70° C. for 4.5 hours. The solution was cooled and adjusted to pH2 with concentrated hydrochloric acid then left standing for 18 hours. Dichloromethane (20 ml) was added and the aqueous basified with potassium carbonate. The organic layer was separated and the aqueous reextracted with dichloromethane (2×10 ml). The combined organics were dried (sodium sulphate) and evaporated to dryness to give a dark yellow oil (192 mg). This oil was dissolved in methanol (2 ml) and sodium methoxide (40 mg, 0.8 mmol) was added. After 2 hours the reaction mixture was evaporated and the residue taken up into dichloromethane (20 ml), washed with water (10 ml), dried (sodium sulphate) then evaporated to dryness to give the crude product which was purified by column chromatography on silica by elution with dichloromethane/methanol (20:1) to give the title compound as a colourless oil (112 mg); m/e 284 (M+); (Found: M+=284.1304, $C_{12}H_{20}N_4O_2S$ requires M+=284.1307); δ (360 MHz, CDCl$_3$) 2.47 (1H, dd, J=3 and 13 Hz) and 2.87–3.03 (5H, m, 2CH$_2$, 6CH$_2$ and 7CH$_2$), 3.15 (1H, s, 4CH), 3.17 (6H, s, N(CH$_3$)$_2$), 3.22 (3H, s, OCH$_3$), 3.27 (3H, s, OCH$_3$), 3.58 (1H, dd, J=7 Hz, 3CH).

c) exo-3-[5-(3-Dimethylamino-1,2,4-thiadiazol)-yl]-1-azabicyclo[2.2.1]heptan-5-one The title compound was obtained (65 mg) as a pale yellow oil from the preceding ketal (105 mg, 0.37 mmol) by the method of Example 17f, except that the reaction mixture was stirred at 65° C. for 3 hours; (Found: M+, 238.0882; $C_{10}H_{14}N_4OS$ requires M+ 238.0888); ν$_{max}$ (liquid film) 1755 cm$^{-1}$ (C=O); δ (360 MHz, CDCl$_3$) 2.92 (1H, dd, J=4 and 18 Hz), 3.04 (1H, s, 4CH), 3.10–3.14 (2H, m), 3.17 (6H, s, N(CH$_3$)$_2$), 3.24–3.40 (3H, m), 3.59 (1H, dd, J=5 and 7 Hz, 3CH).

d) exo-3-[5-(3-Dimethylamino-1,2,4-thiadiazol)-yl]-endo-5-hydroxy-1-azabicyclo[2.2.1]heptane Hemi-Hydrogen Oxalate The title compound free base was obtained (46 mg) as a pale yellow oil from the preceding ketone (52 mg, 0.2 mmol) and sodium borohydride (16 mg, 0.4 mmol) by the method of Example 17 g. The hemi-hydrogen oxalate salt had mp 211°–212° C. (aqueous propan-2-ol); (Found: C, 45.68; H, 5.90; N, 19.02. $C_{10}H_{16}N_4OS.0.5(COOH)_2.0.25H_2O$ requires: C, 45.58; H, 6.08; N, 19.33%); m/e 240 (M+ of free base); δ (360 MHz, D$_2$O) 2.94 (1H, dt, J=3.5 and 10 Hz, 6CH), 3.14 (6H, s, N(CH$_3$)$_2$), 3.26 (1H, d, J=4.5 Hz, 4CH), 3.41 (1H, d, J=10 Hz, 7CH), 3.68 (1H, dd, J=2.5 and 10 Hz, 7CH), 3.76–3.87 (2H, m, 2CH and 6CH), 3.93 (1H, ddd, J=2.8, 5.5 and 12 Hz, 2CH), 4.41 (1H, dd, J=6 and 9 Hz, 3CH), 4.77–4.83 (1H, m, 5CH).

EXAMPLE 34 exo- and endo-3-[5-(3-iso-Propyl-1,2,4-thiadiazol)-yl]-1-azabicyclo[2.2.1]heptane Hydrogen Oxalate Reaction of 3-methoxycarbonyl-1-azabicyclo[2.2.1]heptane (1.25 g, 8.0 mmol) with 5-chloro-3-iso-propyl-1,2,4-thiadiazole (1.70 g, 10.5 mmol) by the method of Example 13 gave:

a) endo-3-[5-(3-iso-Propyl-1,2,4-thiadiazol)-yl]-1-azabicyclo[2.2.1]heptane hydrogen oxalate (531 mg), mp 127° C.; (Found: C, 49.87; H, 6.04, N, 13.36. $C_{11}H_{17}N_3S.(COOH)_2$ requires: C, 49.83; H, 6.11, N, 3.41%); m/e 223 (M+ of free base); δ (360 MHz, D$_2$O) 1.34 (6H, d, J=7.0 Hz, 2×CH$_3$), 1.62–1.71 and 1.99–2.10 (each 1H, each m, 5CH$_2$), 3.34 (1H, septet, J=7.0 Hz, CH(CH$_3$)$_2$), 3.35–3.45 (3H, m, 4CH, one of 6CH$_2$ and one of 7CH$_2$), 3.50 (1H, ddd, J=2.9, 5.1 and 12.0 Hz, one of 6CH$_2$), 3.54–3.59 (1H, m, one of 7CH$_2$), 3.69 (1H, ddd, J=2.3, 5.7 and 12.0 Hz, one of 2CH$_2$), 3.98 (1H, dt, J=2.9 and 12.0 Hz, one of 2CH$_2$), 4.34–4.41 (1H, m, 3CH).

b) exo-3-[5-(3-iso-Propyl-1,2,4-thiadiazol)-yl]-1-azabicyclo[2.2.1]heptane hydrogen oxalate (421 mg), mp 131° C.; (Found: C, 49.77; H, 6.07; N, 13.36. $C_{11}H_{17}N_3S.(COOH)_2$ requires: C, 49.83; H, 6.11; N, 13.41%); m/e 223 (M+ of free base); δ (360 MHz, D$_2$O) 1.32 (6H, d, J=7.0 Hz, 2×CH$_3$), 1.98–2.08 and 2.22–2.32 (each 1H, each m, 5CH$_2$), 3.24–3.43 (4H, m, CH(CH$_3$)$_2$, 4CH, one of 6CH$_2$ and one of 7CH$_2$), 3.48–3.58 (2H, m, one of 6CH$_2$ and one of 7CH$_2$), 3.78–3.85 (2H, m, 2CH$_2$) and 3.93–3.99 (1H, m, 3CH).

EXAMPLE 35

(1R*,6R*) and (1R*,6S*) 6-[5-(3-Cyclopropyl-1,2,4-thiadiazol)-yl]-2-azabicyclo[2.2.2]octane Hydrogen Oxalate a) Methyl 2-t-butyloxycarbonyl-2-azabicyclo[[2.2.2]octane-6-carboxylate Di-t-butyldicarbonate (21.8 g, 0.10 mol) in dry dichloromethane (50 ml) was added dropwise to a stirred, cooled (0° C.) solution of methyl 2-azabicyclo[2.2.2]octane-6-carboxylate (18.2 g, 0.09 mol, mixture of endo and exo isomers, prepared as described in Example 21a, EP 0239309) in dry dichloromethane (100 ml). The resulting solution was stirred at room temperature for 4 hours, water (100 ml) was added and the mixture was stirred for 15 minutes. The organic layer was separated and washed with 0.5M hydrochloric acid (100 ml), water (100 ml), saturated sodium hydrogen carbonate solution (100 ml), water (100 ml) then dried (sodium sulphate) and evaporated to dryness. The residue was purified by column chromatography on silica by elution with ethyl acetate/petroleum ether (60-80) [1:40] to give Isomer A as a colourless oil which crystallised on standing (12.0 g), mp 44°-45° C.; Rf=0.35 in ethyl acetate/petroleum ether (60-80) [1:1] on silica; (Found: C, 62.59; H, 8.55; N, 5.10. $C_{14}H_{23}NO_4$ requires: C, 62.43; H, 8.61; N, 5.20%); $v_{max}$ (film) 1740 and 1695 cm$^{-1}$ (C=O); δ (360 MHz, CDCl$_3$) 1.47 (9H, s C(CH$_3$)$_3$), 1.55-2.20 (7H, m, 4CH, 5CH$_2$, 7CH$_2$ and 8CH$_2$), 2.86-3.00 (1H, m, 6CH), 3.30 (2H, broad s, 3CH$_2$), 3.69 and 3.72 (total 3H, each broad s, CO$_2$CH$_3$, rotamers), 4.21 and 4.38 (total 1H, each broad s, 1CH, rotamers).

Mixed fractions were collected (1:1 mixture, 4.80 g) followed by Isomer B as a colourless oil (6.80 g), Rf=0.32 in ethyl acetate/petroleum ether (60-80) [1:1] on silica; δ (360 MHz, CDCl$_3$) 1.42 and 1.43 (total 9H, each s, C(CH$_3$)$_3$, rotamers), 1.52-2.20 (7H, m, 4CH, 5CH$_2$, 7CH$_2$ and 8CH$_2$), 2.63-2.73 (1H, m, 6CH), 3.19-3.25 (1H, m, 3CH), 3.36-3.42 (1H, m, 3CH), 3.66 and 3.69 (total 3H, each s, CO$_2$CH$_3$, rotamers), 4.27-4.30 and 4.36-4.38 (total 1H, each m, 1CH, rotamers), m/e 269 (M+).

b) 1R*,6R*) and (1R*,6S*) 2 t-Butyloxycarbonyl-6-[5-(3-cyclopropyl-1,2,4-thiadiazol)-yl]-2-azabicyclo[2.2.2]octane A freshly prepared solution of lithium diisopropylamide (prepared from n-butyllithium (8.8 ml of a 1.6M solution) and diisopropylamine (1.96 ml, 14 mmol) in dry tetrahydrofuran (10 ml at −78° C.) was added dropwise to a cooled (−78° C.), stirred solution of the preceding ester (2.50 g, 9.3 mmol, Isomer A) in dry tetrahydrofuran (30 ml) under a nitrogen atmosphere. After 2 hours at −78° C. a solution of 5-chloro-3-cyclopropyl-1,2,4-thiadiazole (2.25 g, 14 mmol) in dry tetrahydrofuran (5 ml) was added dropwise. After 2 hours at −78° C. the reaction mixture was allowed to warm to room temperature over 16 hours and the solvent was removed in vacuo. The residue was treated with methanol (20 ml) and 2M sodium hydroxide solution (20 ml). After 2 hours the solution was washed with ethyl acetate (20 ml) then the aqueous was adjusted to pH1 with concentrated hydrochloric acid and left standing at room temperature for 24 hours. This solution was extracted with diethyl ether (2×20 ml) and the combined organics were dried (sodium sulphate) then evaporated to dryness to give an orange oil (1.70 g) which was purified by column chromatography on silica by elution with ethyl acetate/petroleum ether (60-80) [1:10] to give Isomer A (1R*,6R*) as a pale yellow oil which crystallised on standing (250 mg), mp 90° C.; Rf=0.62 in ethyl acetate/petroleum ether (60-80) [1:1] on silica; (Found: C, 60.82; H, 7.46; N, 12.38. $C_{17}H_{25}N_3SO_2$ requires: C, 60.86; H, 7.51; N, 12.53%); $v_{max}$ (film) 1695 cm$^{-1}$ (C=O); δ (360 MHz, CDCl$_3$) 1.00-1.16 (4H, m, 2×cyclopropyl CH$_2$), 1.49 (9H, s, C(CH$_3$)$_3$), 1.58-1.78 (4H, m), 2.00-2.12 (2H, m) and 2.18-2.36 (2H, m, cyclopropyl CH, 4CH, 5CH$_2$, 7CH$_2$ and 8CH$_2$), 3.39 and 3.40 (total 2H, each broad s, 3CH$_2$, rotamers), 3.58-3.70 (1H, m, 6CH); 4.19 and 4.36 (total 1H, each broad s, 1CH, rotamers).

Isomer B (1R*,6S*) was isolated as a pale yellow oil (660 mg), Rf=0.56 in ethyl acetate/petroleum ether (60-80) [1:1] on silica; (Found: C, 60.84; H, 7.42; N, 12.80. $C_{17}H_{25}N_3SO_2$ requires: C, 60.86; H, 7.51; N, 12.53%); $v_{max}$ (film) 1690 cm$^{-1}$ (C=O); δ (360 MHz, CDCl$_3$) $v_{max}$ 1.00-1.18 (4H, m, 2×cyclopropyl CH$_2$), 1.28 and 1.44 (total 9H, each s, C(CH$_3$)$_3$, rotamers), 1.56-2.36 (8H, m, cyclopropyl CH, 4CH, 5CH$_2$, 7CH$_2$ and 8CH$_2$), 3.32-3.58 (3H, m, 3CH$_2$ and 6CH), 4.11-4.15 (m) and 4.24 (total 1H, broad s, 1CH, rotamers).

c) (1R*,6R*) and (1R*,6S*) 6-[5-(3-Cyclopropyl-1,2,4-thiadiazol)-yl]-2-azabicyclo[2.2.2]octane Hydrogen Oxalate To a cooled (4° C.) solution of (1R*,6R*) 2-t-butyloxycarbonyl-6-[5-(3-cyclopropyl-1,2,4-thiadiazol)-yl]-2-azabicyclo[2.2.2]octane (235 mg, 0.7 mmol) in dichloromethane (5 ml) was added trifluoroacetic acid (1 ml, 14 mmol). After stirring at room temperature for 4 hours water (20 ml) was added and the mixture stirred for 10 minutes. The aqueous layer was separated, basified with potassium carbonate and extracted with ethyl acetate (4×20 ml). The combined organics were dried (Na$_2$SO$_4$) and evaporated to dryness to afford (1R*,6R*) 6-[5-(3-cyclopropyl-1,2,4-thiadiazol)-yl]-2-azabicyclo-[2.2.2]octane free base as a pale yellow oil (140 mg). The hydrogen oxalate salt had mp 165°-168° C. (aqueous propan-2-ol); m/e 235 (M+ of free base); δ (360 MHz, D$_2$O) 1.04-1.16 (4H, m, 2×cyclopropyl CH$_2$), 1.72-2.08 (5H, m, 5CH, 7CH$_2$ and 8CH$_2$), 2.16-2.22 (1H, m, 4CH), 2.30-2.36 (1H, m, cyclopropyl CH), 2.44-2.54 (1H, m, 5CH), 3.28-3.40 (2H, m, 3CH$_2$), 3.84 (1H, broad s, 1CH), 3.90-3.98 (1H, m, 6CH).

(1R*,6S*) 6-[5-(3-cyclopropyl-1,2,4-thiadiazol)-yl]-2-azabicyclo[2.2.2]octane free base (370 mg) was obtained from (1R*,6S*) 2-t-butyloxycarbonyl-6-[5-(3-cyclopropyl-1,2,4-thiadiazol)-yl]-2-azabicyclo-[2.2.2]octane (640 mg, 1.9 mmol) and trifluoroacetic acid (2.9 ml, 38 mmol) as described above. The hydrogen oxalate salt had mp 130°-132° C. (aqueous propan-2-ol); m/e 235 (M+ of free base); δ (360 MHz, D$_2$O) 1.07-1.17 (4H, m, 2×cyclopropyl CH$_2$), 1.80-2.20 (6H, m, 4CH, 5CH, 7CH$_2$ and 8CH$_2$), 2.30-2.48 (2H, m, cyclopropyl CH and 5CH), 3.29 (1H, d, J=12 Hz, 3CH), 3.39 (1H, d, J=12 Hz, 3CH), 3.82-3.90 (2H, m, 1CH and 6CH).

EXAMPLE 36 exo- and endo-3-[5-(3-n-Propyl-1,2,4-thiadiazol)-yl]-1-azabicyclo[2.2.1]heptane Hydrogen Oxalate Reaction of 3-methoxycarbonyl-1-azabicyclo[2.2.1]heptane with 5-chloro-3-n-propyl-1,2,4-thiadiazole by the method of Example 13 gave:

a) endo-3-[5-(3-n-propyl-1,2,4-thiadiazol)-yl]-1-azabicyclo[2.2.1]heptane hydrogen oxalate, mp 145°–147° C.; m/e 223 (M+ free base); δ (360 MHz, D$_2$O) 0.91 (3H, t, J=7.4 Hz, CH$_3$), 1.60–1.70 and 1.98–2.10 (each 1H, each m, 5CH$_2$), 1.79 (2H, sextet, J=7.4 Hz, CH$_2$CH$_3$), 2.96 (2H, t, J=7.4 Hz, CH$_2$CH$_2$CH$_3$), 3.32–3.42 and 3.46–3.58 (3H and 2H respectively, each m, 4CH, 6CH$_2$ and 7CH$_2$), 3.67 (1H, ddd, J=2.3, 5.7 and 12.2 Hz, one of 2CH$_2$), 3.99 (1H, dt, J=3.0 and 12.2 Hz, one of 2CH$_2$) and 4.36–4.44 (1H, m, 3CH).

b) exo-3-[5-(3-n-propyl-1,2,4-thiadiazol)-yl]-1-azabicyclo[2.2.1]heptane hydrogen oxalate, mp 129°–130° C.; m/e 223 (M+of free base); δ (250 MHz, D$_2$O) 0.90 (3H, t, J=7.4 Hz, CH$_3$), 1.78 (2H, sextet, J=7.4 Hz, CH$_2$CH$_3$), 1.95–2.08 and 2.19–2.34 (each 1H, each m, 5CH$_2$), 2.94 (2H, t, J=7.4 Hz, CH$_2$CH$_2$CH$_3$), 3.24–3.45 and 3.47–3.61 (3H and 2H respectively, each m, 4CH, 6CH$_2$ and 7CH$_2$), 3.83 (2H, d, J=7.6 Hz, 2CH$_2$) and 3.98 (1H, t, J=7.6 Hz, 3CH).

EXAMPLE 37 exo- and endo-3-[5-(3-Methoxy-1,2,4-thiadiazol)-yl]-1-azabicyclo[2.2.1]heptane Hydrogen Oxalate Reaction of 3-methoxycarbonyl-1-azabicyclo[2.2.1]heptane with 5-chloro-3-methoxy-1,2,4-thiadiazole by the method of Example 13 gave:

a) endo-3-[5-(3-Methoxy-1,2,4-thiadiazol)-yl]-1-azabicyclo[2.2.1]heptane hydrogen oxalate, mp 113°–114° C.; m/e 211 (M+ of free base); δ (360 MHz, D$_2$O) 1.70–1.80 and 1.98–2.10 (each 1H, each m, 5CH$_2$), 3.30–3.42 and 3.46–3.56 (3H and 2H respectively, each m, 4CH, 6CH$_2$ and 7CH$_2$), 3.62 (1H, ddd, J=2.3, 5.5 and 12.1 Hz, one of 2CH$_2$), 3.91 (1H, dt, J=2.9 and 12.1 Hz, one of 2CH$_2$), 4.09 (3H, s, CH$_3$) and 4.28–4.36 (1H, m, 3CH).

b) exo-3-[5-(3-Methoxy-1,2,4-thiadiazol)-yl]-1-azabicyclo[2.2.1]heptane hydrogen oxalate, (Found: M+=211.0762. C$_9$H$_{13}$N$_3$OS (free base) requires M+=211.0779); δ (250 MHz, D$_2$O) 1.93–2.06 and 2.18–2.35 (each 1H, each m, 5CH$_2$), 3.20–3.45 and 3.48–3.62 (3H and 2H respectively, each m, 4CH, 6CH$_2$ and 7CH$_2$), 3.79 (2H, d, J=7 Hz, 2CH$_2$), 3.90 (1H, t, J=7 Hz, 3CH) and 4.07 (3H, s, CH$_3$).

EXAMPLE 38 exo- and endo-3-[5-(3-Methylthio-1,2,4-thiadiazol)-yl]-1-azabicyclo[2.2.1]heptane Hydrogen Oxalate Reaction of 3-methoxycarbonyl-1-azabicyclo[2.2.1]heptane with 5-chloro-3-methylthio-1,2,4-thiadiazole by the method of Example 13 gave:

a) endo-3-[5-(3-Methylthio-1,2,4-thiadiazol)-yl]-1-azabicyclo[2.2.1]heptane hydrogen oxalate, mp 122°–124° C.; (Found: C, 38.65; H, 4.22; N, 10.63. C$_9$H$_{13}$N$_3$S.2(COOH)$_2$ requires C, 38.32; H, 4.20; N, 10.31%); m/e 227 (M+ of free base); δ (360 MHz, D$_2$O) 1.66–1.78 and 1.98–2.10 (each 1H, each m, 5CH$_2$), 2.69 (3H, s, CH$_3$), 3.32–3.42 and 3.46–3.78 (3H and 2H respectively, each m, 4CH, 6CH$_2$ and 7CH$_2$), 3.68 (1H, ddd, J=2.4, 5.6 and 12.1 Hz, one of 2CH$_2$), 3.93 (1H, td, J=3.0 and 12.1 Hz, one of 2CH$_2$) and 4.36–4.42 (1H, m, 3CH).

b) exo-3-[5-(3-Methylthio-1,2,4-thiadiazol)-yl]-1-azabicyclo[2.2.1]heptane hydrogen oxalate, m/e 227 (M+ of free base); δ (250 MHz, D$_2$O) 1.94–2.07 and 2.12–2.32 (each 1H, each m, 5CH$_2$), 2.67 (3H, s, CH$_3$), 3.20–3.44 and 3.46–3.60 (3H and 2H respectively, each m, 4CH, 6CH$_2$ and 7CH$_2$), 3.75–3.85 (2H, m, 2CH$_2$) and 3.97 (1H, dd, J=5 and 7.5 Hz, 3CH).

EXAMPLE 39

3-[5-(3-n-Propyl-1,2,4-thiadiazol)-yl]-quinuclidine Hydrogen Oxalate

The title compound free base was prepared from 3-methoxycarbonylquinuclidine and 5-chloro-3-n-propyl-1,2,4-thiadiazole by the method described in Example 5. The hydrogen oxalate salt was obtained as a gum, (Found: M+=237.1294. C$_{12}$H$_{19}$N$_3$S (free base) requires M+=237.12996); δ (250 MHz, D$_2$O) 0.91 (3H, t, J=7.4 Hz, CH$_3$), 1.80 (2H, sextet, J=7.4 Hz, CH$_2$CH$_3$), 1.85–1.96 and 2.06–2.30 (each 2H, each m, 5CH$_2$ and 8CH$_2$), 2.50–2.58 (1H, m, 4CH), 2.96 (2H, t, J=7.4 Hz, CH$_2$CH$_2$CH$_3$), 3.28–3.50 (4H, m, 6CH$_2$ and 7CH$_2$), 3.74–3.94 (2H, m, 2CH$_2$) and 4.04–4.14 (1H, m, 3CH).

EXAMPLE 40

(1R*,6R*) and (1R*,6S*) 6-[5-(3-iso-Propyl-1,2,4-thiadiazol)-yl]-2-azabicyclo[2.2.2]octane Hydrogen Oxalate The title compounds were prepared by the method of Example 35 using 5-chloro-3-iso-propyl-1,2,4-thiadiazole to give:

a) (1R*,6R*) 6-[5-(3-iso-Propyl-1,2,4-thiadiazol)-yl]-2-azabicyclo[2.2.2]octane hydrogen oxalate, mp 60°–62° C. (propan-2-ol/diethyl ether); m/e 237 (M+ of free base); δ (250 MHz, D$_2$O) 1.33 (6H, d, J=7 Hz, (CH$_3$)$_2$), 1.66–2.12 (5H, m, 5CH, 7CH$_2$ and 8CH$_2$), 2.14–2.24 (1H, m, 4CH), 2.42–2.58 (1H, m, 5CH), 3.33 (1H, septet, isopropyl CH) overlapped with 3.36 (2H, s, 3CH$_2$), 3.87 (1H, broad s, 1CH) and 3.90–4.04 (1H, m, 6CH).

b) (1R*,6S*) 6-[5-(3-iso-Propyl-1,2,4-thiadiazol)-yl]-2-azabicyclo[2.2.2]octane hydrogen oxalate, (obtained as a 5:1 mixture of isomers), mp 45°–48° C. (propan-2-ol/diethyl ether), m/e 237 (M+ of free base); δ (250 MHz, D$_2$O) 1.34 (6H, d, J=7 Hz, (CH$_3$)$_2$), 1.65–2.24 (6H, m, 4CH, 5CH, 7CH$_2$ and 8CH$_2$), 2.42–2.54 (1H, m, 5CH), 3.32 (1H, d, J=11 Hz, 3CH) overlapped with 3.33 (1H, septet, J=7 Hz, isopropyl CH), 3.37 (1H, d, J=11 Hz, 3CH) and 3.84–4.02 (2H, m, 1CH and 6CH).

EXAMPLE 41

(1R*,6R*) and (1R*,6S*) 6-[5-(3-Ethyl-1,2,4-thiadiazol)-yl]-2-azabicyclo[2.2.2]octane Hydrogen Oxalate The title compounds were prepared by the method of Example 35 using 5-chloro-3-ethyl-1,2,4-thiadiazole to give:

a) (1R*,6R*) 6-[5-(3-Ethyl-1,2,4-thiadiazol)-yl]-2-azabicyclo[2.2.2]octane hydrogen oxalate, mp 151° C. (propan-2-ol); m/e 223 (M+ of free base); δ (250 MHz, D$_2$O) 1.31 (3H, t, J=7.5 Hz, CH$_2$CH$_3$), 1.68–2.10 (5H, m, 5CH, 7CH$_2$ and 8CH$_2$), 2.21 (1H, broad s, 4CH), 2.44–2.58 (1H, m, 5CH), 2.97 (2H, q, J=7.5 Hz, CH$_2$CH$_3$), 3.35 (2H, s, 3CH$_2$), 3.86 (1H, broad s, 1CH) and 3.92–4.00 (1H, m, 6CH).

b) (1R*,6S*) 6-[5-(3-Ethyl-1,2,4-thiadiazol)-yl]-2-azabicyclo[2.2.2]octane hydrogen oxalate (obtained as a 5.7:1 mixture of isomers), mp 58°–59° C.; m/e 223 (M+ of free base); δ (250 MHz, D$_2$O) 1.33 (3H, t, J=7.5 Hz, CH$_2$CH$_3$), 1.76–2.22 (6H, m, 4CH, 5CH, 7CH$_2$ and 8CH$_2$), 2.40–2.54 (1H, m, 5CH), 2.98 (2H, q, J=7.5 Hz, CH$_2$CH$_3$), 3.28 (1H, d, J=12 Hz, 3CH), 3.38 (1H, d, J=12 Hz, 3CH) and 3.84–3.96 (2H, m, 1CH and 6CH).

EXAMPLE 42 exo-3-[5-(3-Isopropyl-1,2,4-thiadiazol)-yl]-endo-5-hydroxy-1-azabicyclo[2.2.1]heptane Hydrogen Oxalate The title compound, prepared by the method described in Example 33 but using 5-chloro-3-iso-propyl-1,2,4-thiadiazole, had mp 175°–180° C.; δ (360 MHz, D$_2$O) 1.34 (6H, d, J=7 Hz, (CH$_3$)$_2$), 2.97 (1H, dt, J=3.5 and 12 Hz, 6CH), 3.29–3.38 (2H, m, isopropyl CH and 4CH), 3.44 (1H, d, J=10 Hz, 7CH), 3.62 (1H, dd, J=3 and 10 Hz, 7CH), 3.78–3.94 (3H, m, 2CH$_2$ and 6CH), 4.57 (1H, dd, J=7 Hz, 3CH) and 4.81–4.86 (1H, m, 5CH).

EXAMPLE 43 exo- and endo-3-[5-(3-Benzyl-1,2,4-thiadiazol)-yl]-1-azabicyclo[2.2.1]heptane

The title compounds were prepared by reaction of 3-methoxycarbonyl-1-azabicyclo[2.2.1]heptane (1.5 g, 9.7 mol) with 3-benzyl-5-chloro-1,2,4-thiadiazole (2.6 g, 12.6 mol) by the method of Example 13. Chromatography on silica eluting with methanoldichloromethane (1:20) gave:

a) endo-3-[5-(3-Benzyl-1,2,4-thiadiazol)-yl]-1-azabicyclo[2.2.1]heptane (330 mg), mp 40°–41° C.; m/e 271 (M$^+$ of free base); δ (360 MHz, CDCl$_3$) 1.22–1.31 and 1.40–1.51 (each 1H, each m, 5CH$_2$), 2.57–2.67, 2.70–2.75 and 2.84–2.95 (2H, 1H and 3H respectively, each m, one of 2CH$_2$, 4CH, 6CH$_2$ and 7CH$_2$), 3.34 (1H, dt, J=3 Hz and 12 Hz, one of 2CH$_2$), 3.63–3.70 (1H, m, 3CH), 4.30 (2H, s, CH$_2$Ph) and 7.19–7.35 (5H, m, Ph).

b) exo-3-[5-(3-Benzyl-1,2,4-thiadiazol)-yl]-1-azabicyclo[2.2.1]heptane (310 mg), mp 35°–36° C.; m/e 271 (M$^+$ of free base); δ (360 MHz, CDCl$_3$) 1.29–1.38 and 1.66–1.76 (each 1H, each m, 5CH$_2$), 2.43 (1H, d, J=7.9 Hz, one of 7CH$_2$), 2.50–2.59 (1H, m, one of 6CH$_2$), 2.73–2.81 (2H, m, 4CH and one of 7CH$_2$), 2.90 (1H, dt, J=4.4 and 11.0 Hz, one of 6CH$_2$), 3.00–3.09 (3H, m, 2CH$_2$ and 3CH), 4.28 (2H, m, CH$_2$Ph) and 7.20–7.36 (5H, m, Ph).

EXAMPLE 44

Tablet Preparation

Tablets containing 1.0, 2.0, 25.0, 26.0, 50.0 and 100.0 mg, respectively, of the following compounds are prepared as illustrated below:

3-[5-(3-Ethyl-1,2,4-thiadiazol)-yl]quinuclidine hydrochloride.
endo-3-[5-(3-Methyl-1,2,4-thiadiazol)-yl]-1-azabicyclo[2.2.1]heptane hydrogen oxalate.
3-[5-(3-Benzyl-1,2,4-thiadiazol)-yl]quinuclidine hydrogen oxalate.
3-[5-(3-Dimethylamino-1,2,4-thiadiazol)-yl]-1,2,5,6-tetrahydropyridine hydrochloride.

| TABLE FOR DOSES CONTAINING FROM 1–25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26–100 MG OF THE ACTIVE COMPOUND | | | |
|---|---|---|---|
| | Amount-mg | | |
| Active Compound | 26.0 | 50.0 | 100.0 |
| Microcrystalline Cellulose | 52.0 | 100.0 | 200.0 |
| Modified food corn starch | 2.21 | 4.25 | 8.5 |
| Magnesium stearate | 0.39 | 0.75 | 1.5 |

All of the active compound, lactose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.00 mg, 50.0 mg and 100.0 mg of active ingredient per tablet.

What is claimed is:

1. A compound represented by formula II:

or a pharmaceutically acceptable salt thereof; wherein R$^1$ represents a non-aromatic azacyclic or azabicyclic ring system; and R$^2$ is selected from the group consisting of, halogen, —CF$_3$, —OR$^7$, —SR$^7$, —NR$^7$R$^8$, —NHOR$^7$, —NHNH$_2$, —CN, —CO$_2$R$^7$, —CONR$^7$R$^8$, C$_{2-4}$ alkenyl, C$_{2-4}$ alkynyl, C$_{3-6}$ cycloalkyl or C$_{1-2}$ alkyl substituted with —OR$^7$, —NR$^7$R$^8$, —SR$^7$, —CO$_2$R$^7$, —CONR$^7$R$^8$ or halogen; wherein R$^7$ and R$^8$ independently represent hydrogen or C$_{1-2}$ alkyl.

2. A compound according to claim 1 wherein R$^2$ is selected from the group consisting of, substituted C$_{1-2}$ alkyl, C$_{3-6}$ cycloalkyl, amino and dimethylamino.

3. A compound according to claim 1 wherein R$^2$ represents a group of formula:

4. A compound selected from the following:
3-[5-(3-phenyl-1,2,4-thiadiazol)-yl]quinuclidine;
3-[5-(3-dimethylamino-1,2,4-thiadiazol)-yl]-quinuclidine;
3-[5-(3-methylmercapto-1,2,4-thiadiazol)-yl]-quinuclidine;
3-[5-(3-cyclopropyl-1,2,4-thiadiazol)-yl]quinuclidine;
3-[5-(3-dimethylamino-1,2,4-thiadiazol)-yl]-1-azabicyclo[2.2.1]heptane;
3-[5-(3-methoxy-1,2,4-thiadiazol)-yl]quinuclidine;
3-[5-(3-cyclopropyl-1,2,4-thiadiazol)-yl]-1-azabicyclo-[2.2.1]heptane;
3-[5-(3-(1-hydroxy-1-phenylmethyl)-1,2,4-thiadiazol)-yl]quinuclidine;
3-[5-(3-benzoyl-1,2,4-thiadiazol)-yl]quinuclidine;
3-[5-(3-(1,1-diphenyl-1-hydroxymethyl)-1,2,4-thiadiazol)-yl]quinuclidine;
1-methyl-3-[5-(3-dimethylamino-1,2,4-thiadiazol)-yl]-1,2,5,6-tetrahydropyridine;
3-[5-(3-dimethylamino-1,2,4-thiadiazol)-yl]-1,2,5,6-tetrahydropyridine;

1-methyl-3-[5-(3-methylamino-1,2,4-thiadiazol)-yl]-1,2,5,6-tetrahydropyridine;
1-methyl-3-[5-(3-ethylamino-1,2,4-thiadiazol)-yl]-1,2,5,6-tetrahydropyridine;
5-[5-(3-dimethylamino-1,2,4-thiadiazol)-yl]-1-azabicyclo[2.2.1]heptan-3-ol;
6-[5-(3-cyclopropyl-1,2,4-thiadiazol)-yl]-2-azabicyclo-[2.2.2]octane;
3-[5-(3-benzyl-1,2,4-thiadiazol)-yl]-1-azabicyclo-[2.2.1]heptane;
1-methyl-3-[5-(3-amino-1,2,4-thiadiazol)-yl]pyrrolidine;
1-methyl-3-[5-(3-amino-1,2,4-thiadiazol)-yl]-1,2,5,6-tetrahydropyridine;
3-[5-(3-amino-1,2,4-thiadiazol)-yl]-1,2,5,6-tetrahydropyridine;
3-[5-(3-amino-1,2,4-thiadiazol)-yl]quinuclidine;
6-[5-(3-amino-1,2,4-thiadiazol)-yl]-1-azabicyclo-[3.2.1]octane;
3-[5-(3-amino-1,2,4-thiadiazol)-yl]-1-azabicyclo-[2.2.1]heptane;
5-[5-(3-amino-1,2,4-thiadiazol)-yl]quinuclidin-3-ol;
5-methyl-3-[5-(3-methyl-1,2,4-thiadiazol)-yl]quinuclidine;
5-[5-(3-amino-1,2,4-thiadiazol)-yl]-1-azabicyclo-[2.2.1]heptan-3-ol;
5-methyl-3-[5-(3-amino-1,2,4-thiadiazol)-yl]-1-azabicyclo[2.2.1]heptane;
3-[5-(3-ethoxy-1,2,4-thiadiazol)-yl]-1-azabicyclo-[2.2.1]heptane;
3-[5-(3-chloro-1,2,4-thiadiazol)-yl]-1-azabicyclo-[2.2.1]heptane;
3-[5-(3-methylamino-1,2,4-thiadiazol)-yl]-1-azabicyclo-[2.2.1]heptane;
3-[5-(3-ethylamino-1,2,4-thiadiazol)-yl]-1-azabicyclo-[2.2.1]heptane;
3-[5-(3-cyclopropyl-1,2,4-thiadiazol)-yl]-1,2,5,6-tetrahydropyridine;
3-[5-(3-benzyl-1,2,4-thiadiazol)-yl]-1,2,5,6-tetrahydropyridine;
3-[5-(3-methoxy-1,2,4-thiadiazol)-yl]-1,2,5,6-tetrahydropyridine;
3-[5-(3-ethoxy-1,2,4-thiadiazol)-yl]-1,2,5,6-tetrahydropyridine;
3-[5-(3-chloro-1,2,4-thiadiazol)-yl]-1,2,5,6-tetrahydropyridine;
3-[5-(3-methylthio-1,2,4-thiadiazol)-yl]-1,2,5,6-tetrahydropyridine;
3-[5-(3-methylamino-1,2,4-thiadiazol)-yl]-1,2,5,6-tetrahydropyridine;
3-[5-(3-ethylamino-1,2,4-thiadiazol)-yl]-1,2,5,6-tetrahydropyridine;
1-methyl-3-[5-(3-cyclopropyl-1,2,4-thiadiazol)-yl]-1,2,5,6-tetrahydropyridine;
1-methyl-3-[5-(3-benzyl-1,2,4-thiadiazol)-yl]-1,2,5,6-tetrahydropyridine;
1-methyl-3-[5-(3-methoxy-1,2,4-thiadiazol)-yl]-1,2,5,6-tetrahydropyridine;
1-methyl-3-[5-(3-methylthio-1,2,4-thiadiazol)-yl]-1,2,5,6-tetrahydropyridine;
5-[5-(3-cyclopropyl-1,2,4-thiadiazol)-yl]-1-azabicyclo[2.2.1]heptan-3-ol;
6-[5-(3-dimethylamino-1,2,4-thiadiazol)-yl]-2-azabicyclo[2.2.2]octane;
and pharmaceutically acceptable thereof.

5. A pharmaceutical composition comprising an effective amount of a compound according to claim 1 in association with a pharmaceutically acceptable carrier.

6. A pharmaceutical composition according to claim 5 further comprising a peripheral cholinergic antagonist.

7. A method for the treatment of neurological and mental disorders due to cholinorgic deficiency which comprises administering to a patient in need of such treatment an effective amount of a compound according to claim 1.

8. A method for the treatment of severe painful conditions which comprises administering to a patient in need of such treatment an effective amount of a compound according to claim 1.

* * * * *